US010806443B2

(12) United States Patent
Norton et al.

(10) Patent No.: US 10,806,443 B2
(45) Date of Patent: Oct. 20, 2020

(54) KNOTLESS SOFT TISSUE DEVICES AND TECHNIQUES

(71) Applicant: Biomet Sports Medicine, LLC, Warsaw, IN (US)

(72) Inventors: Daniel R. Norton, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 137 days.

(21) Appl. No.: 16/160,501

(22) Filed: Oct. 15, 2018

(65) Prior Publication Data

US 2019/0046185 A1 Feb. 14, 2019

Related U.S. Application Data

(63) Continuation of application No. 14/137,350, filed on Dec. 20, 2013, now Pat. No. 10,136,886.

(51) Int. Cl.
*A61B 17/04* (2006.01)
*A61B 17/06* (2006.01)
*A61B 90/92* (2016.01)
*A61B 90/94* (2016.01)

(52) U.S. Cl.
CPC .... *A61B 17/06166* (2013.01); *A61B 17/0401* (2013.01); *A61B 17/0485* (2013.01); *A61B 17/0487* (2013.01); *A61B 90/92* (2016.02); *A61B 90/94* (2016.02); *A61B 2017/0404* (2013.01); *A61B 2017/0406* (2013.01); *A61B 2017/0417* (2013.01); *A61B 2017/0458* (2013.01); *A61B 2017/0495* (2013.01)

(58) Field of Classification Search
CPC ............ A61B 17/0401; A61B 17/0469; A61B 17/0485; A61B 17/0487; A61B 17/06166; A61B 2017/06185; A61B 2017/0409; A61F 2/0811
See application file for complete search history.

(56) References Cited

U.S. PATENT DOCUMENTS

| 65,499 A | 6/1867 | Miller |
|---|---|---|
| 126,366 A | 4/1872 | Wills |
| 233,475 A | 10/1880 | Cook et al. |
| 261,501 A | 7/1882 | Vandermark |

(Continued)

FOREIGN PATENT DOCUMENTS

| AU | 4957264 A | 3/1966 |
|---|---|---|
| AU | 5850469 A | 1/1971 |

(Continued)

OTHER PUBLICATIONS

US 6,238,418 B1, 05/2001, Schwartz (withdrawn)

(Continued)

*Primary Examiner* — Kathleen S Holwerda
(74) *Attorney, Agent, or Firm* — Schwegman Lundberg & Woessner, P.A.

(57) ABSTRACT

A tissue fixation device including a self-locking construct having a first loop, a second loop, and a first free end. A first tail is coupled to, and extends from, the first loop. A second tail is coupled to, and extends from, the second loop. An anchor is coupled to one of the self-locking construct or the first tail such that one of the self-locking construct or the first tail extend through the anchor.

20 Claims, 17 Drawing Sheets

(56) References Cited

U.S. PATENT DOCUMENTS

| | | |
|---|---|---|
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 487,304 A | 12/1892 | Todd |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | Mcknight |
| 3,522,803 A | 8/1970 | Majzlin |
| 3,527,223 A | 9/1970 | Shein |
| 3,533,406 A | 10/1970 | Tatum |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-roel et al. |
| 3,961,632 A | 6/1976 | Moossun |
| 3,973,560 A | 8/1976 | Emmett |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | Mcgrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes |
| 4,144,876 A | 3/1979 | Deleo |
| 4,146,022 A | 3/1979 | Johnson et al. |
| 4,149,277 A | 4/1979 | Bokros |
| 4,157,714 A | 6/1979 | Foltz et al. |

(56) References Cited

U.S. PATENT DOCUMENTS

| | | |
|---|---|---|
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | Difrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland et al. |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | Mcgarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | Mcfarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | Mcquilkin |
| 4,860,513 A | 8/1989 | Whitman |
| 4,863,383 A | 9/1989 | Grafelmann |
| 4,870,957 A | 10/1989 | Goble et al. |
| 4,873,976 A | 10/1989 | Schreiber |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |

(56) References Cited

U.S. PATENT DOCUMENTS

| | | |
|---|---|---|
| 4,978,350 A | 12/1990 | Wagenknecht |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,030,224 A | 7/1991 | Wright |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher |
| 5,129,901 A | 7/1992 | Decoste |
| 5,129,902 A | 7/1992 | Goble et al. |
| 5,129,904 A | 7/1992 | Illi |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | Dipoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |

(56) References Cited

U.S. PATENT DOCUMENTS

| | | |
|---|---|---|
| 5,385,567 A | 1/1995 | Goble |
| 5,391,171 A | 2/1995 | Schmieding |
| 5,391,176 A | 2/1995 | De La Torre |
| 5,391,182 A | 2/1995 | Chin |
| 5,393,302 A | 2/1995 | Clark et al. |
| RE34,871 E | 3/1995 | Mcguire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | Mcleod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott et al. |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | Mcguire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | Mcdevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |

(56) References Cited

U.S. PATENT DOCUMENTS

| | | |
|---|---|---|
| 5,647,874 A | 7/1997 | Hayhurst |
| 5,649,959 A | 7/1997 | Hannam et al. |
| 5,649,963 A | 7/1997 | Mcdevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada |
| 5,690,655 A | 11/1997 | Hart et al. |
| 5,690,676 A | 11/1997 | Dipoto et al. |
| 5,690,678 A | 11/1997 | Johnson |
| 5,693,046 A | 12/1997 | Songer et al. |
| 5,695,497 A | 12/1997 | Stahelin |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal et al. |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | De La Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | Mcdevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | Dipoto et al. |
| 5,961,520 A | 10/1999 | Beck, Jr. et al. |
| 5,961,521 A | 10/1999 | Roger |
| 5,961,524 A | 10/1999 | Crombie |
| 5,964,764 A | 10/1999 | West, Jr. et al. |

(56) References Cited

U.S. PATENT DOCUMENTS

| | | |
|---|---|---|
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | Mckernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan et al. |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo |
| 6,193,754 B1 | 2/2001 | Seedhom |
| 6,200,318 B1 | 3/2001 | Har-shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |

(56) References Cited

U.S. PATENT DOCUMENTS

| | | |
|---|---|---|
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | Mcdevitt |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'addario |
| 6,544,281 B2 | 4/2003 | Elattrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B2 | 4/2003 | Jacob |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Järvinen |
| 6,565,572 B2 | 5/2003 | Chappius |
| 6,565,573 B1 | 5/2003 | Ferrante |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | Lovuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |

(56) References Cited

U.S. PATENT DOCUMENTS

| | | |
|---|---|---|
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 | 9/2004 | Monnet |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | Mcdevitt et al. |
| 6,833,005 B1 | 12/2004 | Mantas |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | Tenhuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | Mcdevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris |
| 7,118,578 B2 | 10/2006 | West, Jr. et al. |
| 7,118,583 B2 | 10/2006 | O'quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,695,503 B1 | 4/2010 | Kaiser |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,264 B2 | 1/2011 | Mcdevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |

(56) References Cited

U.S. PATENT DOCUMENTS

| | | |
|---|---|---|
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,932,331 B2 | 1/2015 | Kaiser et al. |
| 8,936,621 B2 | 1/2015 | Denham et al. |
| 8,968,364 B2 | 3/2015 | Berelsman |
| 8,998,949 B2 | 4/2015 | Stone et al. |
| 9,005,287 B2 | 4/2015 | Stone |
| 9,017,381 B2 | 4/2015 | Kaiser et al. |
| 10,136,886 B2 | 11/2018 | Norton et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood, Jr. et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | Elattrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller, III |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | Mcdevitt et al. |
| 2003/0135214 A1 | 7/2003 | Fetto |
| 2003/0135239 A1 | 7/2003 | Gabriel et al. |
| 2003/0135963 A1 | 7/2003 | Holbrook et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown, Jr. et al. |
| 2004/0024457 A1 | 2/2004 | Boyce et al. |
| 2004/0039389 A1 | 2/2004 | West, Jr. et al. |
| 2004/0044391 A1 | 3/2004 | Porter |
| 2004/0059357 A1 | 3/2004 | Koseki |

(56) References Cited

U.S. PATENT DOCUMENTS

| | | |
|---|---|---|
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | Mcdevitt et al. |
| 2004/0182968 A1 | 9/2004 | Gentry |
| 2004/0187314 A1 | 9/2004 | Johnson |
| 2004/0193185 A1 | 9/2004 | Mcbrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach, III |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer, Jr. |
| 2005/0064042 A1 | 3/2005 | Vunjak-novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090828 A1 | 4/2005 | Alford |
| 2005/0090862 A1 | 4/2005 | Mcdevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'driscoll et al. |
| 2005/0137600 A1 | 6/2005 | Jacobs et al. |
| 2005/0137624 A1 | 6/2005 | Fallman |
| 2005/0149033 A1 | 7/2005 | Mcguire et al. |
| 2005/0149122 A1 | 7/2005 | Mcdevitt et al. |
| 2005/0149187 A1 | 7/2005 | Clark et al. |
| 2005/0159812 A1 | 7/2005 | Dinger, III et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller, III |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West, Jr. |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant et al. |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |

(56) References Cited

U.S. PATENT DOCUMENTS

| | | |
|---|---|---|
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz, III |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone |
| 2006/0293709 A1 | 12/2006 | Bojarski et al. |
| 2007/0005080 A1 | 1/2007 | Wolniewicz, III et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0038218 A1 | 2/2007 | Grevious |
| 2007/0043371 A1 | 2/2007 | Teague |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | Elattrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250059 A1 | 10/2007 | Weisshaupt et al. |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | Mcdevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-may |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | Mcdevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teaguex et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1* | 12/2009 | Stone ............... A61B 17/0401 606/228 |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | Dimatteo et al. |
| 2011/0026141 A1 | 2/2011 | Barrows |

(56) References Cited

U.S. PATENT DOCUMENTS

| | | |
|---|---|---|
| 2011/0046733 A1 | 2/2011 | Eggli |
| 2011/0087284 A1 | 4/2011 | Stone et al. |
| 2011/0098727 A1 | 4/2011 | Kaiser et al. |
| 2011/0106153 A1* | 5/2011 | Stone .................. A61B 17/823 606/228 |
| 2011/0112537 A1 | 5/2011 | Bernstein et al. |
| 2011/0112538 A1 | 5/2011 | Dell'oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | Mcdevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | Mcdevitt et al. |
| 2012/0245585 A1 | 9/2012 | Kaiser et al. |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone |
| 2013/0035722 A1 | 2/2013 | Mcdevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0173754 A1 | 6/2015 | Norton et al. |

FOREIGN PATENT DOCUMENTS

| | | |
|---|---|---|
| AU | 5963869 A | 2/1971 |
| AU | 1505470 A | 11/1971 |
| AU | 2223767 A | 5/1973 |
| AU | 3615171 A | 5/1973 |
| AU | 440266 B2 | 9/1973 |
| AU | 5028569 A | 9/1973 |
| AU | 7110887 A | 10/1987 |
| AU | 639410 A | 11/1989 |
| AU | 651929 B2 | 8/1994 |
| DE | 2529669 A1 | 3/1976 |
| DE | 2747312 A1 | 4/1979 |
| DE | 2818254 A1 | 10/1979 |
| DE | 2919009 A1 | 11/1979 |
| DE | 3027138 A1 | 12/1981 |
| DE | 3225620 A1 | 2/1983 |
| DE | 3136083 A1 | 3/1983 |
| DE | 233303 A1 | 2/1986 |
| DE | 4127550 A1 | 2/1993 |
| DE | 4302397 A | 7/1993 |
| DE | 29621340 U1 | 4/1998 |
| DE | 19841252 A1 | 3/2000 |
| DE | 20207781 U1 | 8/2002 |
| EP | 0019062 A1 | 11/1980 |
| EP | 0108912 A2 | 5/1984 |
| EP | 0129422 A2 | 12/1984 |
| EP | 0129442 A1 | 12/1984 |
| EP | 0172130 A2 | 2/1986 |
| EP | 0241240 A2 | 10/1987 |
| EP | 0241792 A1 | 10/1987 |
| EP | 0260970 A2 | 3/1988 |
| EP | 0270704 A1 | 6/1988 |
| EP | 0282789 A2 | 9/1988 |
| EP | 0315371 A2 | 5/1989 |
| EP | 0317406 A1 | 5/1989 |
| EP | 0340159 A1 | 11/1989 |
| EP | 0346183 A1 | 12/1989 |
| EP | 0349173 A1 | 1/1990 |
| EP | 0374088 A1 | 6/1990 |
| EP | 0409364 A2 | 1/1991 |
| EP | 0415915 A1 | 3/1991 |
| EP | 0440991 A1 | 8/1991 |
| EP | 0441065 A2 | 8/1991 |
| EP | 0451932 A1 | 10/1991 |
| EP | 0464480 A1 | 1/1992 |
| EP | 0490417 A1 | 6/1992 |
| EP | 0497079 A1 | 8/1992 |
| EP | 0502509 A1 | 9/1992 |
| EP | 0502698 A1 | 9/1992 |
| EP | 520177 A1 | 12/1992 |
| EP | 0546726 A1 | 6/1993 |
| EP | 0574707 A1 | 12/1993 |
| EP | 0582514 A1 | 2/1994 |
| EP | 0591991 A2 | 4/1994 |
| EP | 0599219 A2 | 5/1994 |
| EP | 0611551 A1 | 8/1994 |
| EP | 0627203 A2 | 12/1994 |
| EP | 0651979 A1 | 5/1995 |

(56) References Cited

FOREIGN PATENT DOCUMENTS

| | | |
|---|---|---|
| EP | 0669110 A2 | 8/1995 |
| EP | 0686373 A1 | 12/1995 |
| EP | 0702933 A1 | 3/1996 |
| EP | 0775473 A1 | 5/1997 |
| EP | 0913123 A1 | 5/1999 |
| EP | 0913131 A2 | 5/1999 |
| EP | 0995409 A1 | 4/2000 |
| EP | 1013229 A2 | 6/2000 |
| EP | 1093773 A1 | 4/2001 |
| EP | 1093774 A1 | 4/2001 |
| EP | 1555945 A2 | 7/2005 |
| EP | 2238944 A2 | 10/2010 |
| EP | 2544607 A1 | 1/2013 |
| EP | 2709557 A1 | 3/2014 |
| FR | 2622790 A1 | 5/1989 |
| FR | 2655840 A1 | 6/1991 |
| FR | 2682867 A1 | 4/1993 |
| FR | 2687911 A1 | 9/1993 |
| FR | 2688689 A1 | 9/1993 |
| FR | 2704140 A3 | 10/1994 |
| FR | 2717070 A1 | 9/1995 |
| FR | 2723528 A1 | 2/1996 |
| FR | 2744010 A1 | 8/1997 |
| FR | 2745999 A1 | 9/1997 |
| FR | 2770764 A1 | 5/1999 |
| GB | 401677 A | 11/1933 |
| GB | 1413477 A | 11/1975 |
| GB | 1485681 A | 9/1977 |
| GB | 2083751 A | 3/1982 |
| GB | 2118474 A | 11/1983 |
| GB | 2227175 A | 7/1990 |
| GB | 2253147 A | 9/1992 |
| GB | 2312376 A | 10/1997 |
| GB | 2403416 A | 1/2005 |
| JP | 5362911 A | 7/1987 |
| JP | 62159647 A | 7/1987 |
| JP | 62295657 A | 12/1987 |
| JP | 5269160 A | 10/1993 |
| JP | 5300917 A | 11/1993 |
| JP | 751292 A | 2/1995 |
| JP | 10211213 A | 8/1998 |
| JP | 5362912 B2 | 12/2013 |
| JP | 5374942 B2 | 12/2013 |
| JP | 5378230 B2 | 12/2013 |
| WO | WO 8300615 A1 | 3/1983 |
| WO | WO-8603666 A1 | 7/1986 |
| WO | WO-8701270 A1 | 3/1987 |
| WO | WO-8901767 A1 | 3/1989 |
| WO | WO-8909030 A1 | 10/1989 |
| WO | WO-8910096 A1 | 11/1989 |
| WO | WO-9008510 A1 | 8/1990 |
| WO | WO-9203980 A1 | 3/1992 |
| WO | WO-9314705 A1 | 8/1993 |
| WO | WO-9315694 A1 | 8/1993 |
| WO | WO-9502373 A1 | 1/1995 |
| WO | WO-9503003 A1 | 2/1995 |
| WO | WO-9529637 A1 | 11/1995 |
| WO | WO-9532670 A1 | 12/1995 |
| WO | WO-9609797 A1 | 4/1996 |
| WO | WO-9629029 A1 | 9/1996 |
| WO | WO-9737603 A1 | 10/1997 |
| WO | WO-9812991 A1 | 4/1998 |
| WO | WO-9812992 A | 4/1998 |
| WO | WO-9822047 A1 | 5/1998 |
| WO | WO-9822048 A1 | 5/1998 |
| WO | WO-9901084 A2 | 1/1999 |
| WO | WO-9912480 A1 | 3/1999 |
| WO | WO-9937219 A1 | 7/1999 |
| WO | WO-9944544 A1 | 9/1999 |
| WO | WO-9952472 A1 | 10/1999 |
| WO | WO-0040159 A1 | 7/2000 |
| WO | WO-0139671 A1 | 6/2001 |
| WO | WO-0236020 A1 | 5/2002 |
| WO | WO-03005914 A1 | 1/2003 |
| WO | WO-03071962 A2 | 9/2003 |
| WO | WO-03077772 A1 | 9/2003 |
| WO | WO-03092551 A1 | 11/2003 |
| WO | WO-2004091412 A | 10/2004 |
| WO | WO-05104992 A1 | 11/2005 |
| WO | WO-2005122954 A1 | 12/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014100109 A1 | 6/2014 |
| WO | WO-2014151766 A1 | 9/2014 |

OTHER PUBLICATIONS

"AperFix® System Surgical Technique Guide. Single Tunnel Double Bundle.™" Cayenne Medical brochure, (Aug. 2008), 8 pgs.

"U.S. Appl. No. 14/137,350, Final Office Action dated Jun. 19, 2018", 9 pgs.

"U.S. Appl. No. 14/137,350, Final Office Action dated Aug. 14, 2017", 10 pgs.

"U.S. Appl. No. 14/137,350, Non Final Office Action dated Jan. 24, 2018", 10 pgs.

"U.S. Appl. No. 14/137,350, Non Final Office Action dated Mar. 17, 2017", 9 pgs.

"U.S. Appl. No. 14/137,350, Notice of Allowance dated Sep. 18, 2018", 8 pgs.

"U.S. Appl. No. 14/137,350, Response filed Jan. 11, 2017 to Restriction Requirement dated Nov. 21, 2016", 7 pgs.

"U.S. Appl. No. 14/137,350, Response filed Apr. 24, 2018 to Non Final Office Action dated Jan. 24, 2018", 10 pgs.

"U.S. Appl. No. 14/137,350, Response filed Jun. 19, 2017 to Non Final Office Action dated Mar. 17, 2017", 10 pgs.

"U.S. Appl. No. 14/137,350, Response filed Aug. 14, 2018 to Final Office Action dated Jun. 19, 2018", 10 pgs.

"U.S. Appl. No. 14/137,350, Response filed Dec. 5, 2017 to Final Office Action dated Aug. 14, 2017", 10 pgs.

"U.S. Appl. No. 14/137,350, Restriction Requirement dated Nov. 21, 2016", 7 pgs.

"Arthroscopic Meniscal Repair using the Meniscal Cinch™", Surgical Technique brochure. Arthrex®, 6 sheets, (2008), 6 sheets.

"Bio-Intrafix (TCP/PLA) & Intrafix, Tibial Soft Tissue Fasteners", DePuy Mitek, ((date unknown)), 6 pgs.

"Biomechanical Evaluation of the Biomet Sports Medicine JurggerKnot™ Soft Anchor in Porcine Bone", Study completed Jan. 2010. Biomet Sports Medicine Research and Develoment, Warsaw, Indiana, (Jan. 2010), 2 pgs.

"Do your next distal tendon repair with . . . The Lubbers Technique", Teno Fix® brochure, Ortheon® Medical, (2003), 2 pgs.

"Ez Loc Femoral Fixation Device", copyright 2005 Arthrotek, Inc, (2005), 8 pgs.

"International Application Serial No. PCT/US2011/026349, International Preliminary Report on Patentability dated Sep. 20, 2012", 11 pgs.

"International Application Serial No. PCT/US2011/026349, International Search Report dated Jul. 28, 2011", 6 pgs.

"International Application Serial No. PCT/US2011/026349, Invitation to Pay Additional Fees dated Jun. 9, 2011", 5 pgs.

"International Application Serial No. PCT/US2011/026349, Written Opinion dated Jul. 28, 2011",9 pgs.

"International Application Serial No. PCT/US2011/038188, International Preliminary Report on Patentability dated Dec. 6, 2012", 14 pgs.

(56) References Cited

OTHER PUBLICATIONS

"International Application Serial No. PCT/US2011/038188, International Search Report dated Oct. 14, 2011", 6 pgs.
"International Application Serial No. PCT/US2011/038188, Invitation to Pay Additional Fees dated Aug. 5, 2011", 5 pgs.
"International Application Serial No. PCT/US2011/038188, Written Opinion dated Oct. 14, 2011", 12 pgs.
"International Application Serial No. PCT/US2012/037703, International Preliminary Report on Patentability dated Nov. 28, 2013", 10 pgs.
"International Application Serial No. PCT/US2012/037703, International Search Report dated Sep. 21, 2012", 6 pgs.
"International Application Serial No. PCT/US2012/037703, Invitation to Pay Additional Fees dated Jul. 19, 2012".
"International Application Serial No. PCT/US2012/037703, Written Opinion dated Sep. 21, 2012", 8 pgs.
"International Application Serial No. PCT/US2012/062738, International Search Report dated Mar. 6, 2013", 6 pgs.
"International Application Serial No. PCT/US2012/062738, Written Opinion dated Mar. 6, 2013", 7 pgs.
"International Application Serial No. PCT/US2012/064832, International Preliminary Report on Patentability dated May 30, 2014", 9 pgs.
"International Application Serial No. PCT/US2012/064832, International Search Report dated Feb. 6, 2013", 3 pgs.
"International Application Serial No. PCT/US2012/064832, Written Opinion dated Feb. 6, 2013", 7 pgs.
"International Application Serial No. PCT/US2013/075989, International Search Report dated Mar. 6, 2014", 4 pgs.
"International Application Serial No. PCT/US2013/075989, Written Opinion dated Mar. 6, 2014", 7 pgs.
"International Application Serial No. PCT/US2014/026413, International Search Report dated Jun. 6, 2014", 5 pgs.
"International Application Serial No. PCT/US2014/026413, Written Opinion dated Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.
"Make your next tendon repair an open-and-shut case. The Teno Fix® Tendon Repair System", Teno Fix® brochure, Ortheon® Medical, (2003), 2 pgs.
"Next Generation in Knee Ligament Reconstruction & Repair Technology", Suture Tensioner w/Tensiometer, Arthrex®, Inc. catalog, (2009).
"Panalok Anchor with PDS II and ETHIBOND Suture", Mitek Products ETHICON, (1997), 2 pgs.
"Rapid Sternal Closure", KLS Martin L.P., [Online] retrieved from the internet: USPTO Private Pair, U.S. Appl. No. 13/645,964 , (2006).
"Rotator Cuff Fixation", Acufex Fastenator System: Shoulder Arthroscopy, H-2-H-22.
"SE Graft Tensioning System Surgical Technique", Linvatec Corporation copyright 2003, (2004), 12 pgs.

"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Fromm, Stuart M.D. E, "", Rapidloc, Meniscal Repair System, Mitek Products, Ethicon, (2001), 6 pgs.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, MD, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.
Saxena, Pankaj, et al., "Use of Double Wires in Sternal Closure, A Useful Technique", Texas Heart® Institute. Journal List> Tex Heart Inst J > v.33(4), (2006).
Smith, et al., "Endoscopic Meniscal Repair Using the T-Fix", (1996), 16 pgs.
Smith, et al., "Fast-Fix", Meniscal Repair System;, (2001), 3 pgs.
Thomas, Roseberg D, "Technique for ACL Reconstruction with Acufex Director Drill Guide and Endobutton CL", Smith & Nephew, Technique Guide. (1999), 18 pgs.
Weiler, A, et al., "Biodegradierbare Interferenzschrauben in der Kreuzbandchirurgie", Opjournal 14, (1998), 278-284.
Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.

\* cited by examiner

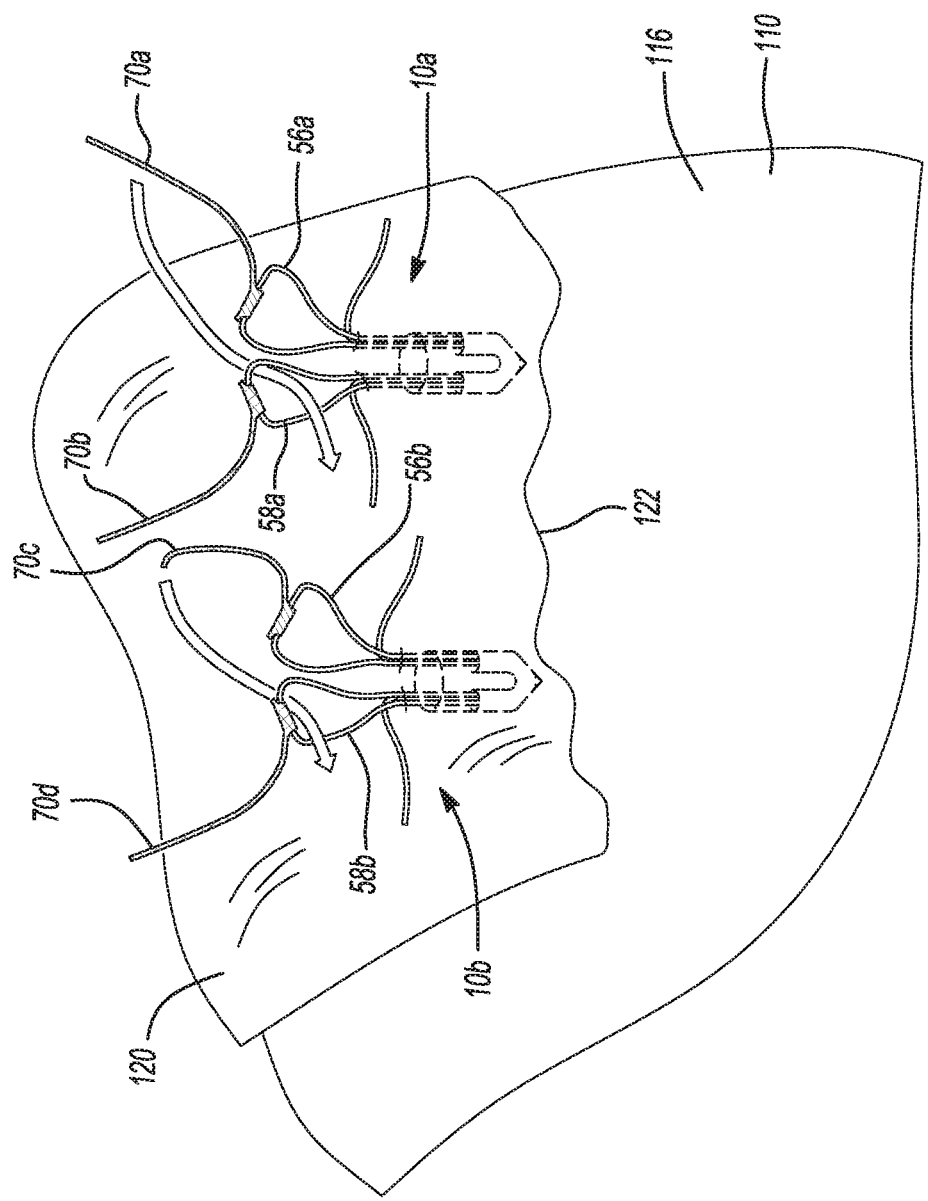

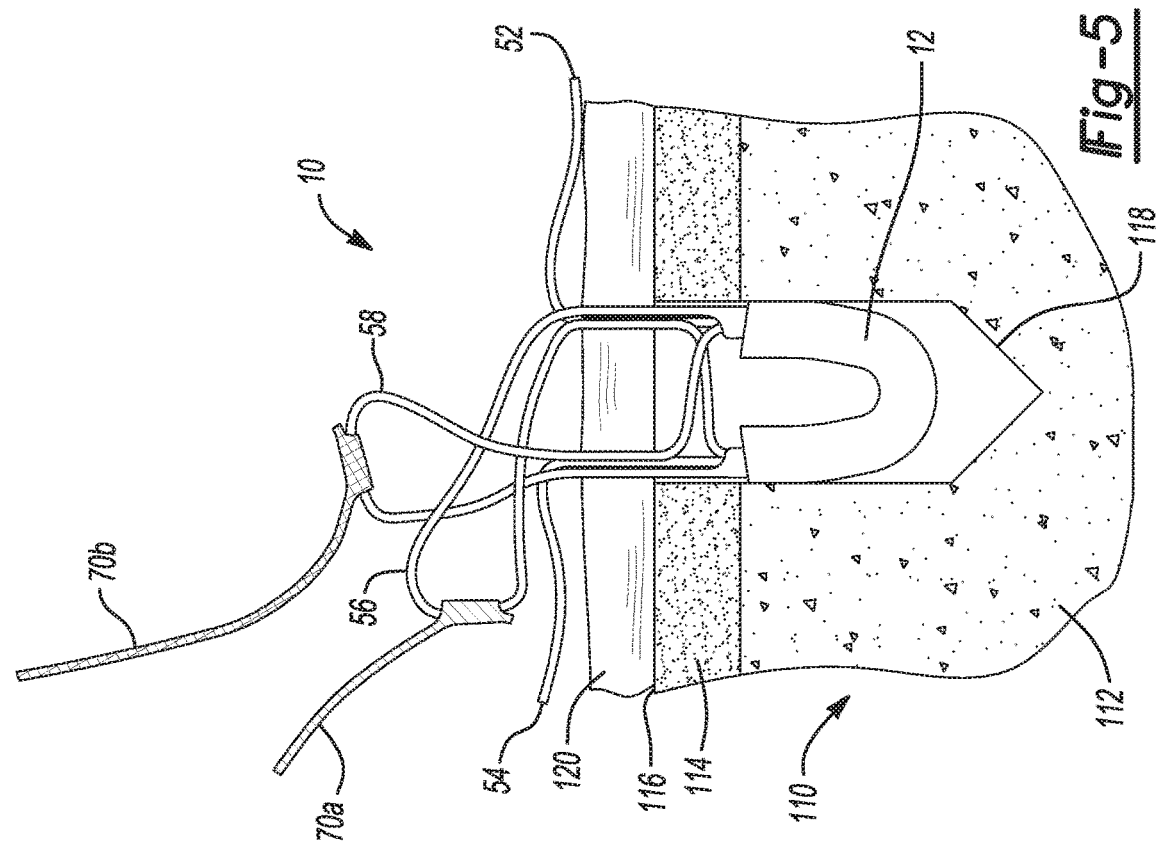
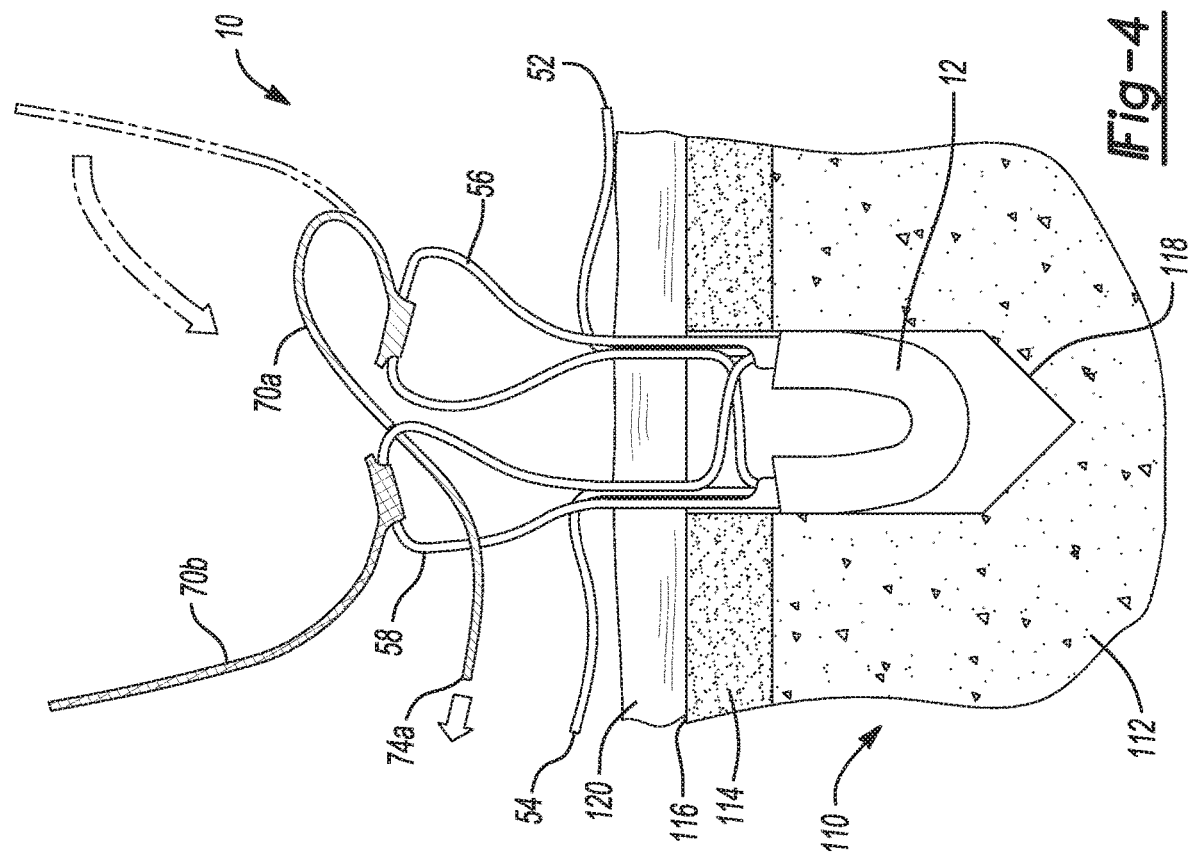

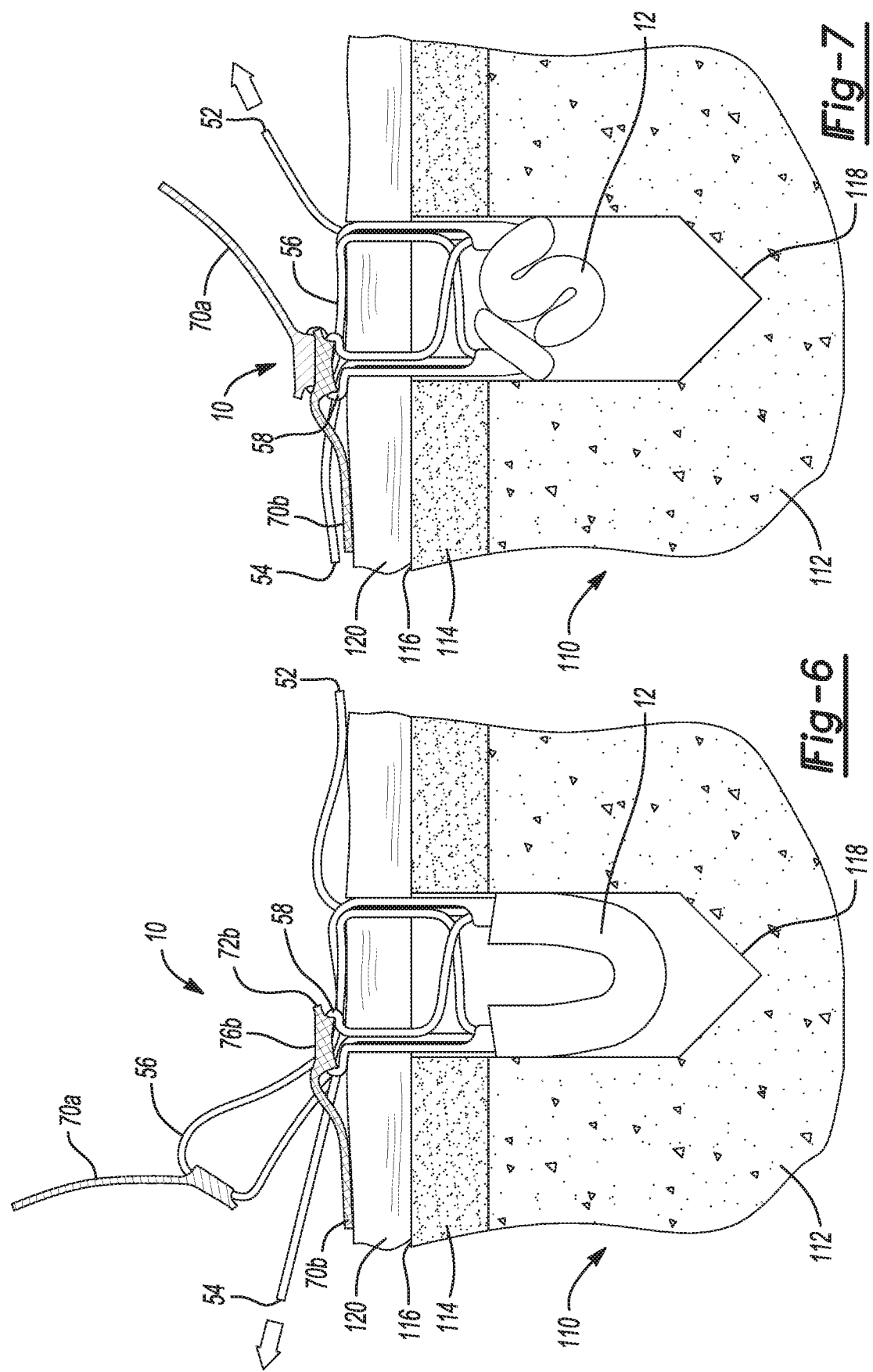

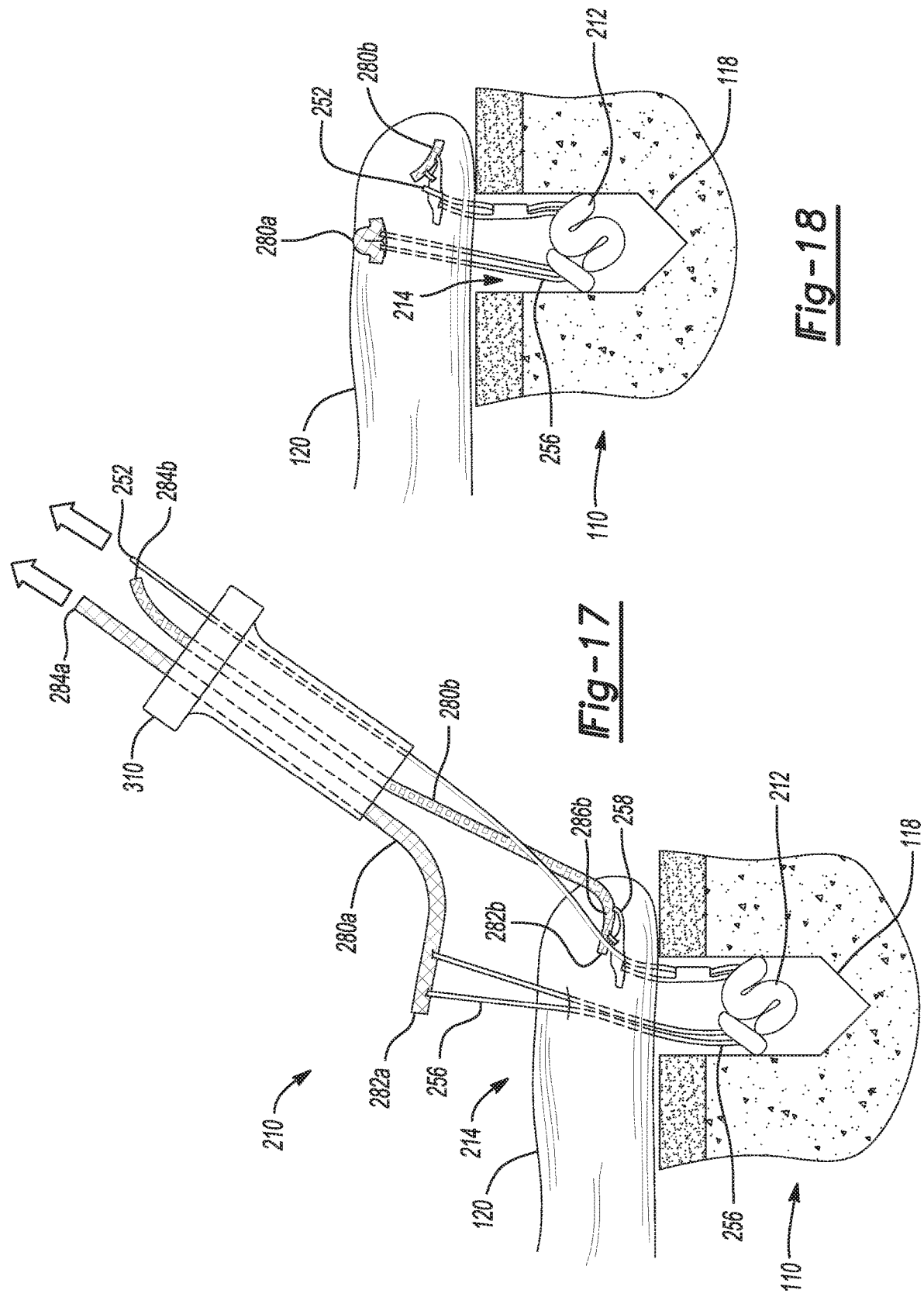

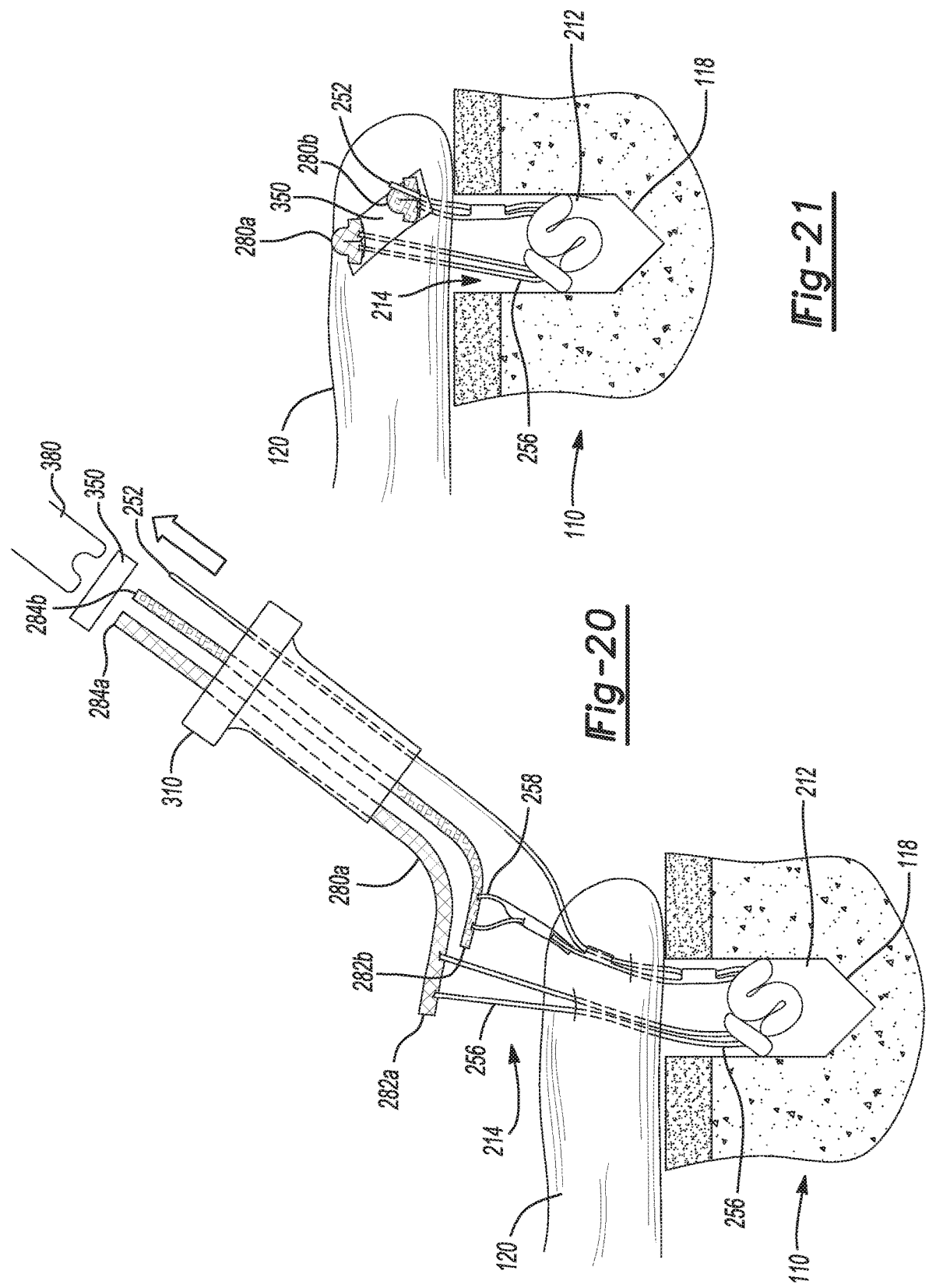

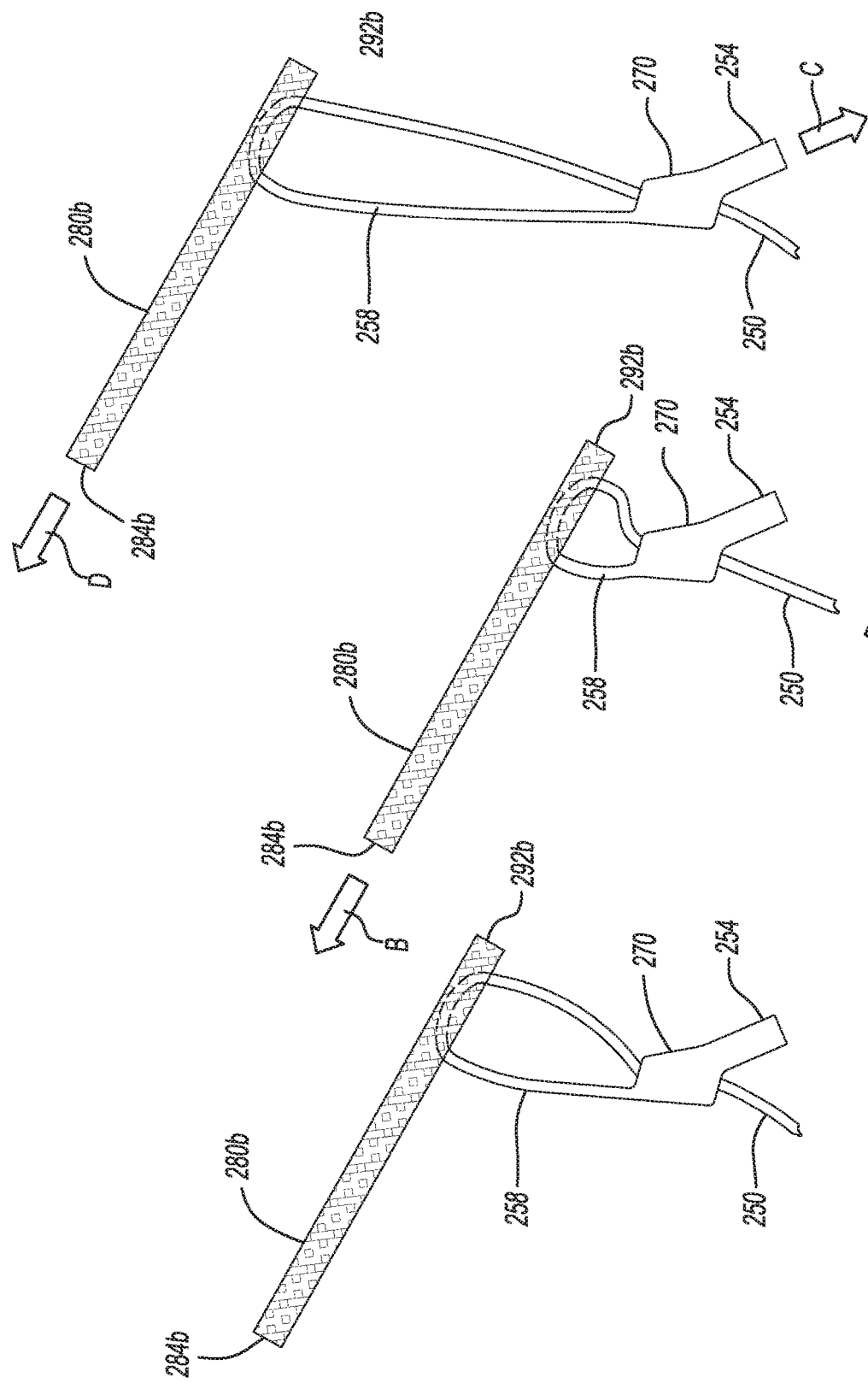

KNOTLESS SOFT TISSUE DEVICES AND TECHNIQUES

FIELD

The present disclosure relates to knotless soft tissue devices and techniques.

BACKGROUND

This section provides background information related to the present disclosure, which is not necessarily prior art.

Arthroscopic procedures often include sutures and anchors to secure soft tissue to bone, secure bone pieces together, and to secure separated portions of soft tissue together. Despite their widespread use, sutures and suture anchors, as well as methods for their use, can be improved. For example, tying sutures into knots may be very time consuming and difficult to perform, particularly inside the joint space. As a result, the cost of the procedure may increase and the capacity of the surgeon may be limited. Furthermore, the strength of the repair may be limited by the strength of the knot. The methods and devices disclosed herein address these issues and numerous others.

SUMMARY

This section provides a general summary of the disclosure, and is not a comprehensive disclosure of its full scope or all of its features.

The present teachings provide for a tissue fixation device including a self-locking construct having a first loop, a second loop, and a first free end. A first tail is coupled to, and extends from, the first loop. A second tail is coupled to, and extends from, the second loop. An anchor is coupled to one of the self-locking construct or the first tail such that one of the self-locking construct or the first tail extend through the anchor.

The present teachings also provide for a tissue fixation device including a self-locking construct having a first loop and a free end. A first tail is coupled to, and extends from, the first loop. A second tail is coupled to, and extending from, the self-locking construct. An anchor is coupled to the first tail such that the self-locking construct extends through the anchor.

The present teachings also provide for a method for securing soft tissue to bone. The method includes implanting a first anchor into bone, the first anchor coupled to one of a first loop of a first self-locking construct or a first tail mounted to the first loop. The first tail and a portion of the first loop are passed through the tissue. The first tail is passed through a second loop and the first loop is partially passed through the second loop on a side of the tissue opposite to the bone. A first free end of the first self-locking construct is pulled to close the first loop.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 illustrates two of the tissue fixation devices of FIG. 1 implanted in bone to affix tissue relative to the bone;

FIGS. 4-8 illustrate use of the tissue fixation device of FIG. 1 to fix the tissue to bone;

FIGS. 14-18 illustrate use of the tissue fixation device of FIG. 13 to affix tissue to bone;

FIGS. 20 and 21 illustrate use of a braided strip to facilitate securing tissue to bone; and FIGS. 22A-22C illustrate a tail of either one of the tissue fixation devices of FIGS. 12 and 13 coupled to a loop of the tissue fixation devices, and use of the tail to open the loop.

Corresponding reference numerals indicate corresponding parts throughout the several views of the drawings.

DETAILED DESCRIPTION

Example embodiments will now be described more fully with reference to the accompanying drawings.

Figure 1:
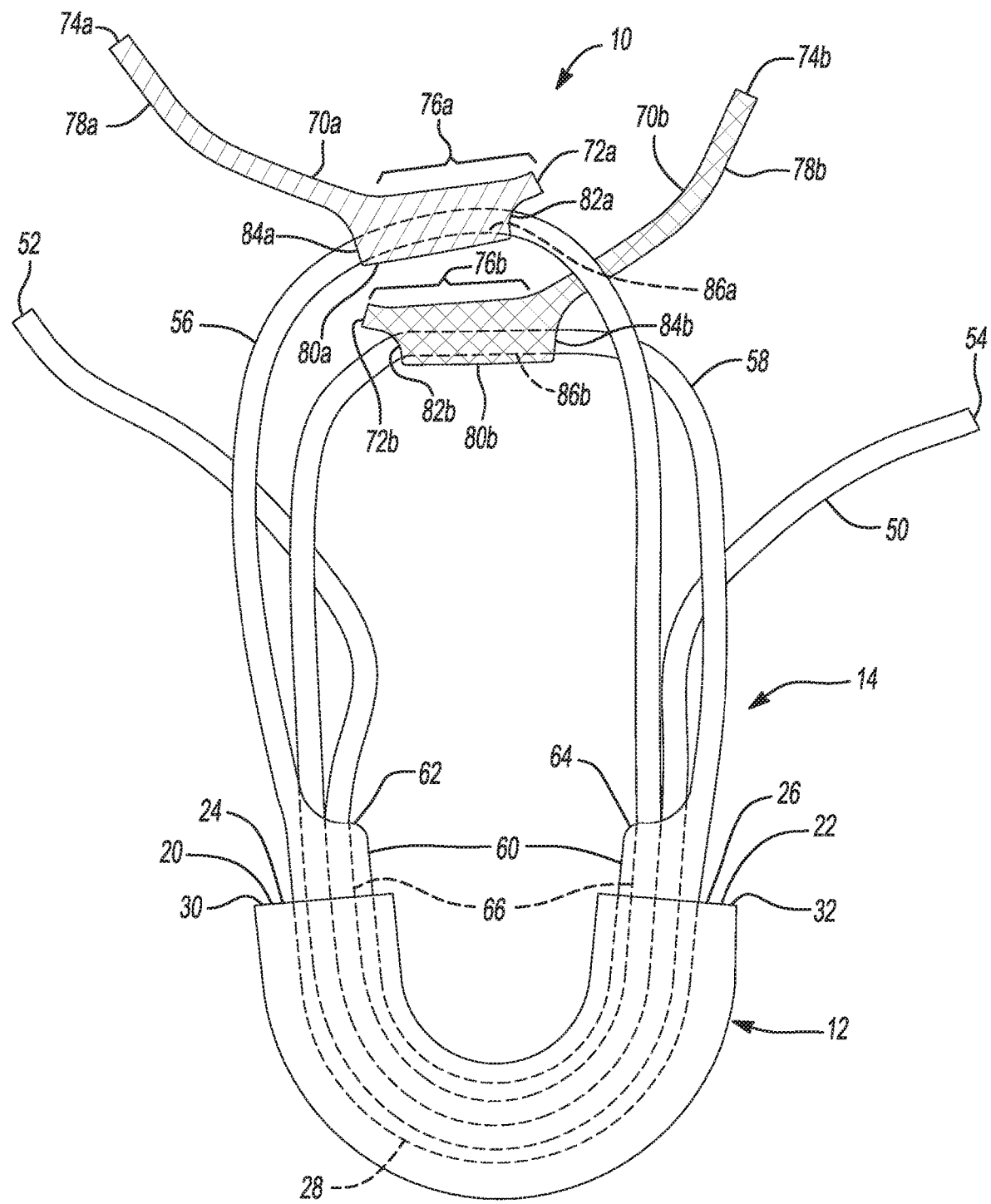
FIG. 1 illustrates a tissue fixation device according to the present teachings.

With initial reference to FIG. 1, a tissue fixation device according to the present teachings is generally illustrated at reference numeral 10. Although the tissue fixation device 10 is generally described herein as configured to secure tissue to bone, the tissue fixation device 10 can also be used to, for example, secure two bones or bone portions together, as well as two tissues or tissue portions together. The tissue fixation device 10 generally includes a soft or flexible anchor 12 and a self-locking construct 14.

The anchor 12 includes a first anchor end 20 and a second anchor end 22, which is opposite to the first anchor end 20. The anchor 12 can be an elongate member having a sleeve or tubular configuration. The anchor 12 thus defines a first opening 24 at the first anchor end 20, and defines a second opening 26 at the second anchor end 22. The anchor 12 further defines an anchor internal passage 28 extending between the first opening 24 and the second opening 26. At the first anchor end 20 is a first end surface 30, and at the second anchor end 22 is a second end surface 32. As described herein, the first and the second end surfaces 30 and 32 are configured to abut an interior surface of cortical bone in order to facilitate retention of the tissue fixation device 10 within a bone hole.

In place of the anchor 10, any suitable soft or hard anchor can be used, such as any of the soft or hard anchors described in U.S. application Ser. No. 13/098,927 ("'927 application") titled "Method and Apparatus for Soft Tissue Fixation," filed on May 2, 2011, and assigned to Biomet Sports Medicine, LLC, which is incorporated herein by reference. In place of the anchor 10 can also be any of the anchors described in U.S. Pat. No. 8,562,647 ('647 patent") titled "Method and Apparatus for Securing Soft Tissue to Bone," issued on Oct. 22, 2013, and assigned to Biomet Sports Medicine, LLC, which is incorporated herein by reference. The anchor 12 can be made of any suitable material, such as resorbable or non-resorbable materials, including braided suture, sponges, and sponge-like materials, including braided suture, sponges, and sponge-like materials in solid form, perforated materials, woven/braided from biocompatible materials or fibers, such as, for example, polymer, polyester, polyethylene, cotton, silk, or other natural or synthetic materials.

The self-locking construct 14 can be made of any suitable material, such as a flexible material including suture, such as a suture strand 50. When the construct 14 is made of suture, any suitable suture can be used. For example, a braided hollow-core suture strand 50 can be used. Any suitable braided suture can be used, such as any of the braided sutures disclosed in U.S. patent application Ser. No. 12/915, 962 titled "Method and Apparatus for Securing Soft Tissue to Bone," which was filed on Oct. 29, 2010, published as Publication No. 2011/0098727 on Apr. 28, 2011, and is assigned to Biomet Sports Medicine, LLC. Although the construct 14 can be made of any suitable material in addition to suture, the construct 14 will generally be described herein as a construct.

The construct 14 generally includes a first end 52 and a second end 54 of the suture strand 50. The suture strand 50 is arranged to provide a self-locking, first adjustable loop 56 and a self-locking, second adjustable loop 58. The suture strand 50 includes a portion 60 between the first end 52 and the second end 54. The portion 60 itself includes a first end 62 and a second end 64. The portion 60 defines a passageway or internal passage portion 66 extending between the first end 62 and the second end 64 of the portion 60.

As illustrated in FIG. 1, portions of the suture strand 50 extend through the internal passage portion 66. The suture strand 50 passes through the internal passage portion 66 a first time to define the first adjustable loop 56, and a second time to define the second adjustable loop 58. The internal passage portion 66 can be any suitable passage through the suture strand 50, through which portions of the suture strand 50 can pass to define the first and the second adjustable loops 56 and 58, such as the passage portions described in the '927 application and the '647 patent, which are incorporated herein by reference.

Slidably mounted to the first adjustable loop 56 is a first suture tail 70a. Slidably mounted to the second adjustable loop 58 is a second suture tail 70b. The first suture tail 70a is similar to the second suture tail 70b. In order to facilitate differentiation between the first suture tail 70a and the second suture tail 70b, such as by a surgeon in the operating room, the first suture tail 70a and the second suture tail 70b can include any suitable distinguishing identifiers. For example, the first and second suture tails 70a and 70b can be provided with different colors, different visual patterns, different indicia (such as different striping) different sizes (such as different lengths or widths), or different materials.

The first suture tail 70a and the second suture tail 70b can each be made of any suitable material, such as the same material as the suture strand 50, or any of the alternative materials of the suture strand 50 described above. Features in common between the first and second suture tails 70a and 70b are illustrated and described using similar reference numbers, but reference numbers of the first suture tail 70a include the suffix "a," and reference numbers of the second suture tail 70b include the suffix "b." Because the first suture tail 70a is similar to the second suture tail 70b, the detailed description below of the first suture tail 70a describes the second suture tail 70b as well.

The first suture tail 70a includes a first end 72a and a second end 74a. The first end 72a is opposite to the second end 74a. At the first end 72a is a locking portion 76a. Extending from the locking portion 76a to the second end 74a is an elongated tail portion 78a. The locking portion 76a includes a portion 80a, which defines a passageway or passage portion 86a. The passage portion 86a extends between a first opening 82a and a second opening 84a formed between suture braids of the first suture tail 70a. The first adjustable loop 56 extends through the passage portion 86a, thereby coupling the first suture tail 70a to the suture strand 50. Similarly, the second suture tail 70b can be arranged such that the suture strand 50 of the second adjustable loop 58 extends through passageway 86b defined by the second suture tail 70b at the locking portion 76b.

As further described herein, the construct 14 is configured such that upon pulling the first end 52 of the suture strand 50, a portion of the suture strand 50 within the internal passage portion 66 will be pulled out through the first sleeve end 62 thereof, thus closing the first adjustable loop 56, and reducing the size thereof. Similarly, pulling the second end 54 pulls a portion of the suture strand 50 out of the internal passage portion 66 at the second sleeve end 64, in order to reduce the size of, and close, the second adjustable loop 58. As the first and second ends 52 and 54 are pulled, the first and second adjustable loops 56 and 58 are tensioned, thus causing the internal passage portion 66 to collapse onto portions of the suture strand 50 extending therethrough, thereby restricting movement of the suture strand 50 through the sleeve internal passage 66, and thus locking the first and second adjustable loops 56 and 58 to prevent them from reopening. In this manner, the first and the second adjustable loops 56 and 58 are self-locking.

Prior to the tissue fixation device 10 being implanted, the first and second adjustable loops 56 and 58 can be provided in a retracted or closed position, such that the first and second adjustable loops 56 and 58 are small, which can advantageously reduce any possibility of tangling of the first and second adjustable loops 56 and 58. In order to open the first and second adjustable loops 56 and 58, the first suture tail 70a can be pulled at the second end 74a, thereby pulling a portion of the suture strand 50 out from within the internal passage portion 66 at the second sleeve end 64. The second adjustable loop 58 can be opened by pulling the second suture tail 70b, such as at the second end 74b, in order to pull a portion of the suture strand 50 out from within the internal passage portion 66 at the first sleeve end 62. Because the first and the second adjustable loops 56 and 58 have not yet been tensioned, such as when closed against tissue 120 to secure the tissue 120 to bone 110 as described herein, and the anchor 12 has not yet collapsed as illustrated in FIG. 7 for example, the first and the second adjustable loops 56 and 58 can be opened in this manner.

Figure 2:
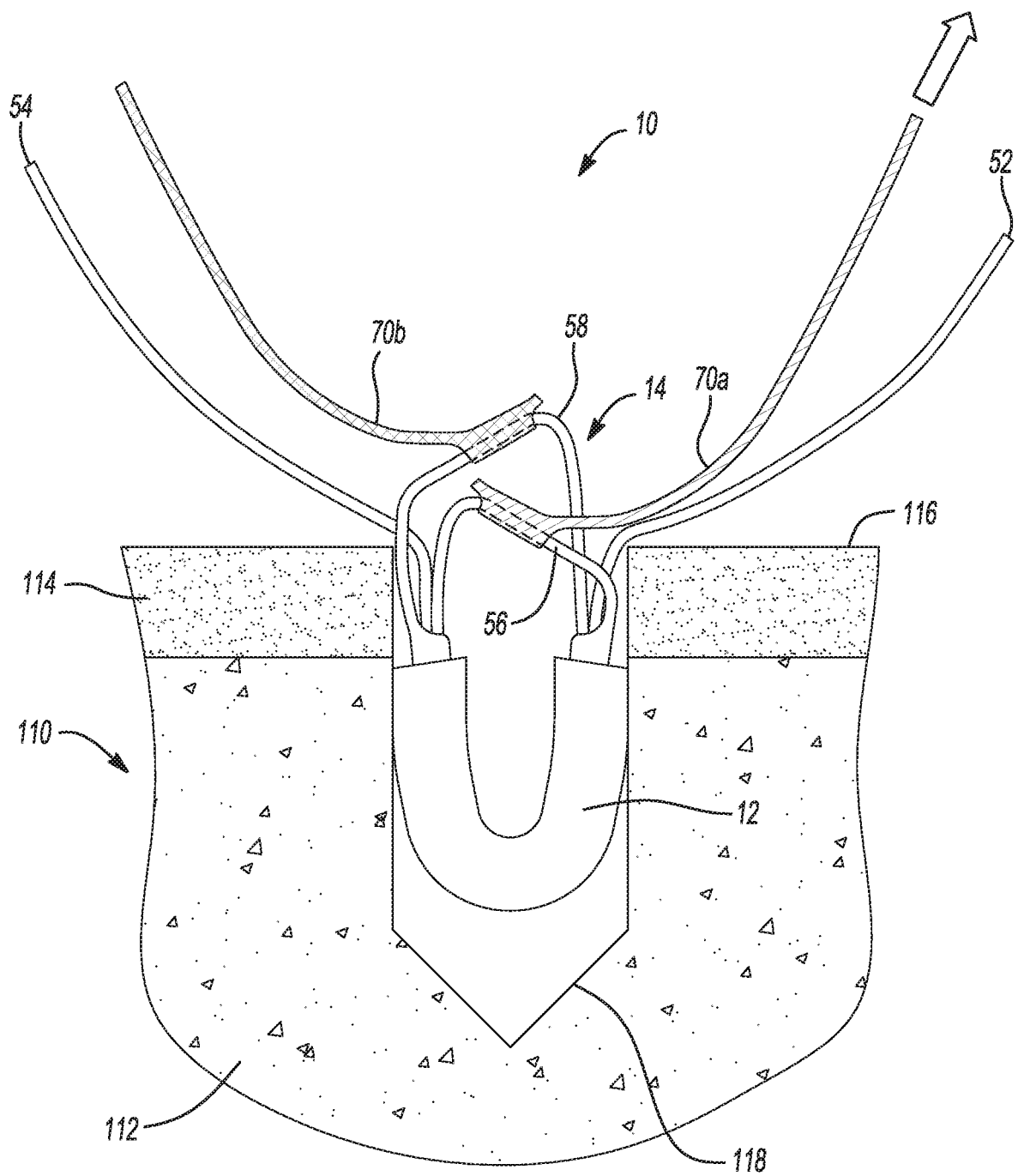
FIG. 2 illustrates the tissue fixation device of FIG. 1 in bone.

With reference to FIG. 2, the tissue fixation device 10 is illustrated implanted in bone 110. The bone 110 includes a relatively soft inner cancellous bone layer 112, and a relatively hard outer cortical bone layer 114. An outer surface 116 of the bone 110 is at a side of the cortical bone layer 114 opposite to the cancellous bone layer 112. Formed within the bone 110 is a bone hole 118. The bone hole 118 is formed through the outer surface 116, through the outer cortical bone layer 114, and into the cancellous bone layer 112. The bone hole 118 can be formed in any suitable manner, such as with a suitable drill or impactor, or any other suitable bone cutting device.

The tissue fixation device 10 is arranged such that the anchor 12 is seated in the bone hole 118. The anchor 12 protrudes slightly into the cancellous bone layer 112 proximate to the cortical bone layer 114 at the first and second anchor ends 20 and 22 thereof. The first and the second end surfaces 30 and 32 abut the cortical bone layer 114 at a side thereof opposite to the outer surface 116 and adjacent to the cancellous bone layer 112. As illustrated in FIG. 2, the first and second adjustable loops 56 and 58 are made smaller or closed, so as to reduce any possibility of tangling, as described above. After one or more of the tissue fixation devices 10 are implanted in bone, they may be used to secure tissue 120 to bone 110, as will now be described.

With reference to FIG. 3, two of the tissue fixation devices 10 are illustrated implanted in the bone 110 in the same manner as illustrated in FIG. 2. The tissue fixation devices 10 can be used to secure tissue 120 to the bone 110. The two tissue fixation devices 10 are illustrated as first tissue fixation device 10a and second tissue fixation device 10b. Only the first tissue fixation device 10a need be used to secure tissue 120 to bone 110. To enhance fixation of the tissue 120 to bone 110, however, additional tissue fixation devices 10 can be used, such as the second tissue fixation device 10b or yet additional tissue fixation devices 10, as described herein.

The second tissue fixation device 10b is substantially similar to, or the same as, the first tissue fixation device 10a. The second tissue fixation device 10b includes first and second suture tails 70c and 70d, which are similar to, or the same as, the first and second suture tails 70a and 70b of the first tissue fixation device 10a. The first and second adjustable loops of the second tissue fixation device 10b are illustrated at reference numerals 56b and 58b respectively.

After the tissue fixation devices 10a and 10b are initially seated in the bone hole 118 as illustrated in FIG. 2, their suture tails 70a, 70b, 70c, and 70d are pulled through the tissue 120, as illustrated in FIG. 3. The tails 70a, 70b, 70c, and 70d and the loops 56a, 58a, 56b, and 58b are then arranged as described below and illustrated in FIGS. 4-7 to apply pressure against the tissue 120 and secure the tissue 120 against the outer bone surface 116.

FIGS. 4-7 illustrate arrangement of the first and second tails 70a and 70b, and the first and second loops 56a and 56b, of tissue fixation device 10 (illustrated in FIG. 3 at reference number 10a to distinguish the second tissue fixation device 10b) to retain the tissue 120 against the outer bone surface 116. The method of FIGS. 4-7 applies to both the first and second tissue fixation devices 10a and 10b of FIG. 3.

After the tissue fixation device 10 has been seated in the bone hole 118 as illustrated in FIG. 2, the first and second suture tails 70a and 70b are pulled through the tissue 120, thus pulling the first and second adjustable loops 56 and 58 through the tissue 120 as well, as initially set forth above. The first and second suture tails 70a and 70b, and the first and second adjustable loops 56 and 58 associated therewith, are pulled through spaced apart areas of the tissue 120, thus leaving a portion of the tissue 120 between the first and second adjustable loops 56 and 58.

With reference to FIG. 4, after the first and second adjustable loops 56 and 58 are pulled through the tissue 120 using the first and second suture tails 70a and 70b, the first and second adjustable loops 56 and 58 can be coupled together and cinched down against the tissue 120 in order to secure the tissue against the outer surface 116 of the bone 110. For example, the second end 74a of the first suture tail 70a can be pulled through the second adjustable loop 58 in order to pull the first suture tail 70a through the second adjustable loop 58, and pull the first adjustable loop 56 such that a portion thereof extends through the second adjustable loop 58, as illustrated in FIG. 5.

With reference to FIG. 6, the second adjustable loop 58 is cinched down onto the first adjustable loop 56 by pulling on the second end 54. As the second end 54 is pulled, the second adjustable loop 58 will reduce in size and pull the first adjustable loop 56 against the tissue 120, and affix the tissue 120 to the outer surface 116 of the bone 110. With reference to FIG. 7, after the size of the second adjustable loop 58 is reduced, the size of the first adjustable loop 56 is reduced by pulling the first end 52 of the suture strand 50. As the first adjustable loop 56 is reduced in size, the first suture tail 70a will abut the second suture tail 70b and/or the second adjustable loop 58. As the first end 52 is pulled further, the first suture tail 70a and/or the first adjustable loop 56 will pull the second suture tail 70b and the second adjustable loop 58 further against the tissue 120, in order to further secure the tissue 120 to the outer surface 116 of the bone 110. As the first and second ends 52 and 54 are pulled as illustrated in FIGS. 6 and 7 respectively, the first and second adjustable loops 56 and 58 are tensioned, thus causing the internal passage portion 66 to collapse onto portions of the suture strand 50 extending therethrough, thereby restricting movement of the suture strand 50 through the internal passage portion 66, and thus locking the first and second adjustable loops 56 and 58 to prevent them from reopening. The anchor 12 will then deform as illustrated in FIG. 7 to lock the anchor 12 in the bone hole 118.

Figure 8:
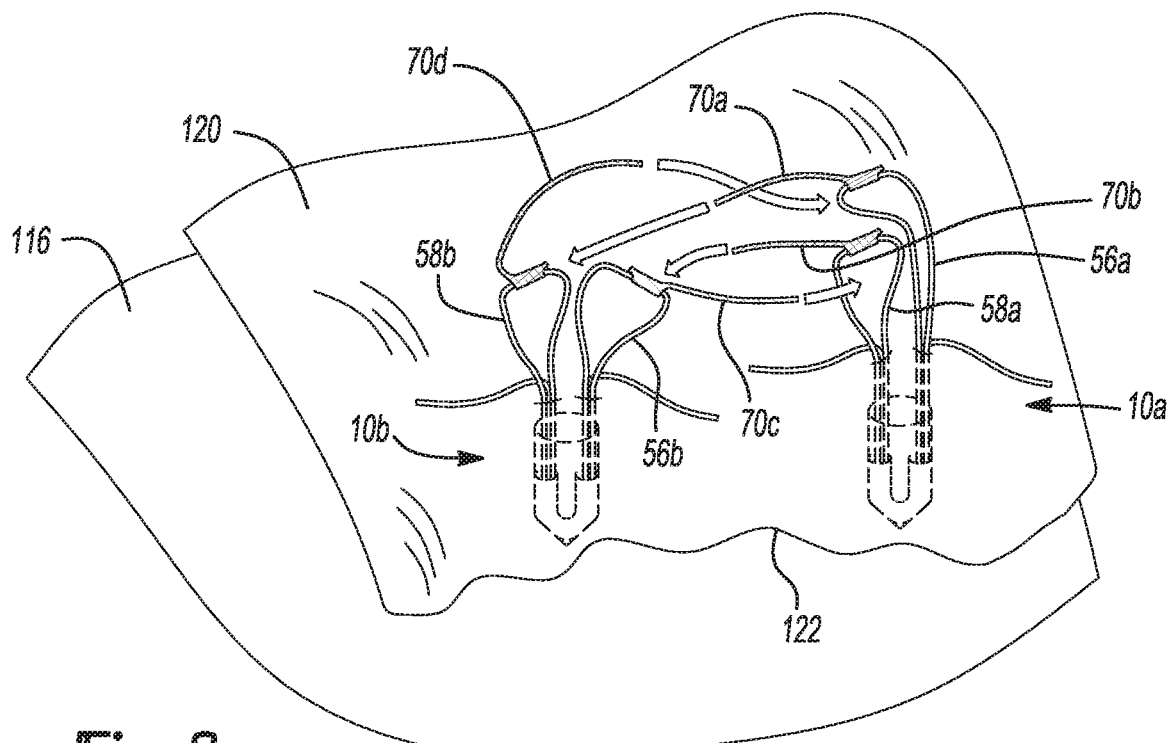

Although FIGS. 3-7 illustrate coupling together first and second adjustable loops 56 and 58 from the same tissue fixation device 10, various other configurations and arrangements are contemplated. For example, and with reference to FIG. 8, in applications where both the first tissue fixation device 10a and the second tissue fixation device 10b are used, the first suture tail 70a of the first tissue fixation device 10a can be coupled to the second tissue fixation device 10b. This can be done by inserting the first suture tail 70a through the second adjustable loop 58b of the second tissue fixation device 10b, which will couple the first adjustable loop 56a of the first tissue fixation device 10a to the second adjustable loop 58b of the second tissue fixation device 10b once the second adjustable loop 58b is cinched down onto the first adjustable loop 56a in the same manner described above. Similarly, the second adjustable loop 58b of the second tissue fixation device 10b can be coupled to the first adjustable loop 56a of the first tissue fixation device 10a by closing the second adjustable loop 58a onto the first adjustable loop 56b as described above. Use of both the first and second tissue fixation devices 10a and 10b to fix the tissue 120 to the bone 110 advantageously retains a greater portion of the tissue 120 against the bone 110, thereby distributing load against the tissue 120 and decreasing any possibility of the suture strands 50 cutting through the tissue 120.

Figure 9:
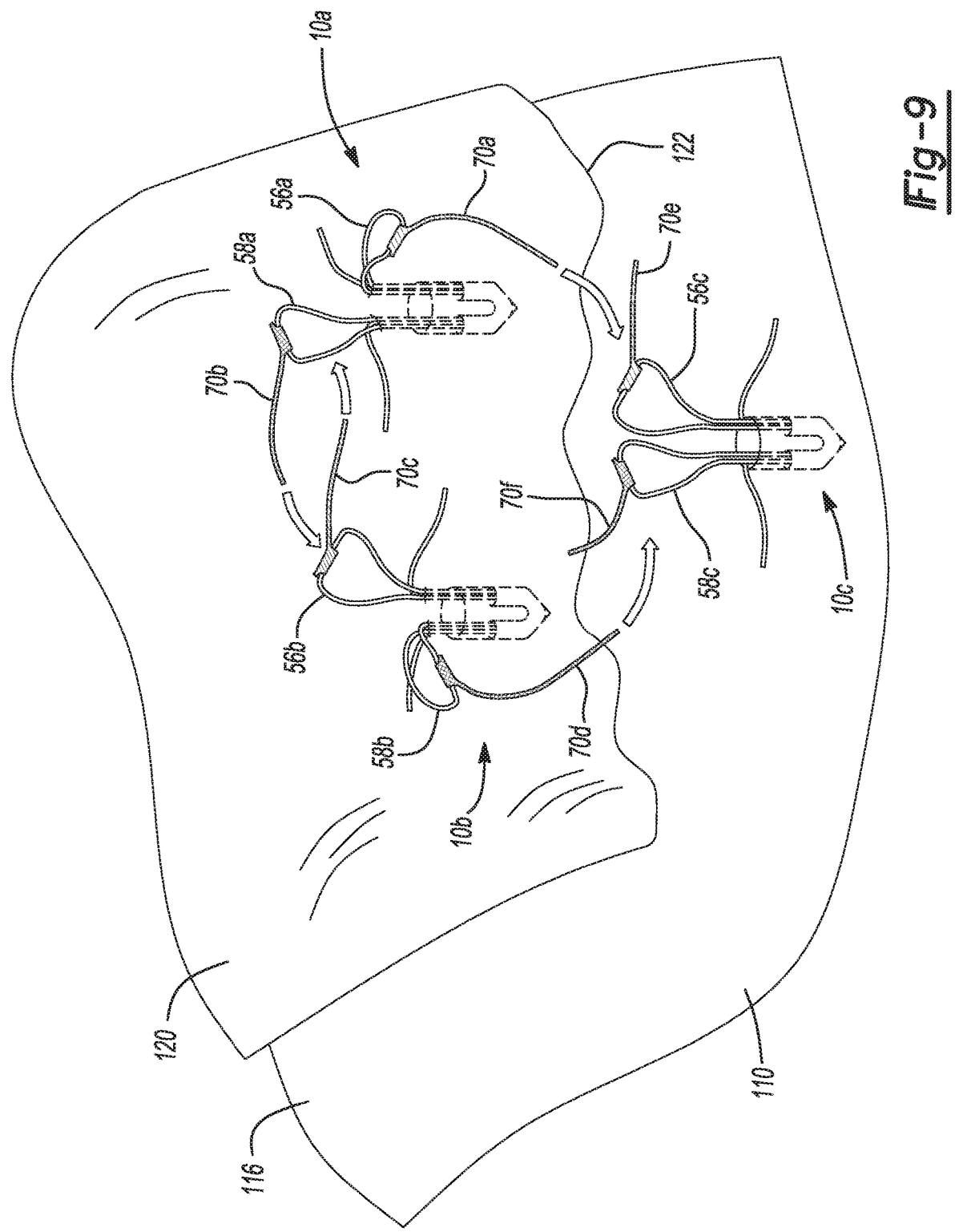
FIG. 9 illustrates three of the tissue fixation devices of FIG. 1 implanted in bone for affixing tissue to bone.

With reference to FIG. 9, a third tissue fixation device 10c can be used to affix the tissue 120 to the bone 110. The third tissue fixation device 10c can be similar to, or the same as, the first and second tissue fixation devices 10a and 10b. The third tissue fixation device 10c can be implanted in the bone 110 spaced apart from the tissue 120, and beyond a distal end 122 thereof.

The third tissue fixation device 10c can be coupled with the first and second tissue fixations device 10a and 10b in any suitable manner. For example, the first suture tail 70a of the first tissue fixation device 10a can be inserted through a first adjustable loop 56c of the third tissue fixation device 10c in order to couple the first adjustable loops 56a and 56c together after the first adjustable loop 56c is cinched down onto the first adjustable loop 56a of the first tissue fixation device 10a. The second adjustable loop 58c of the third tissue fixation device 10c can be coupled to the second adjustable loop 58b of the second tissue fixation device 10b, such as by inserting the second suture tail 70d through the second adjustable loop 58c and closing the second adjustable loop 58c onto the second adjustable loop 58b. The first and second tissue fixation devices 10a and 10b can be connected by coupling the second adjustable loop 58a of the first tissue fixation device 10a with the first adjustable loop 56b of the second tissue fixation device 10b as described above. Thus, the suture tails 70a-70f are coupled to loops 56a-56c and 58a-58c of neighboring tissue fixation devices 10a-10c in order to chain the tissue fixation devices 10a-10c together. Including the third tissue fixation device 10c in the arrangement of FIG. 9 advantageously secures the distal end 122 of the tissue 120 to the outer surface 116 of the bone 110.

Figure 10:
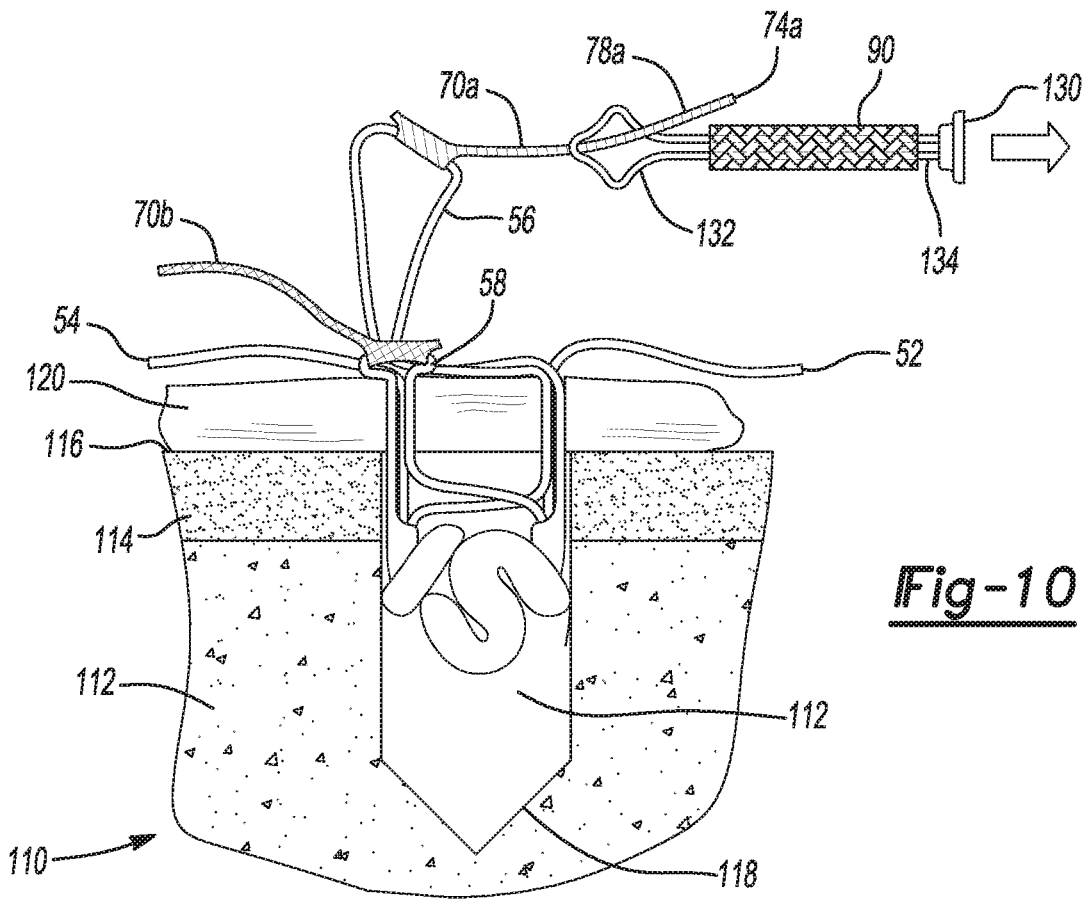
FIG. 10 illustrates the tissue fixation device of FIG. 1 implanted in bone, and an additional flexible anchor being added to the fixation device.
Figure 11:
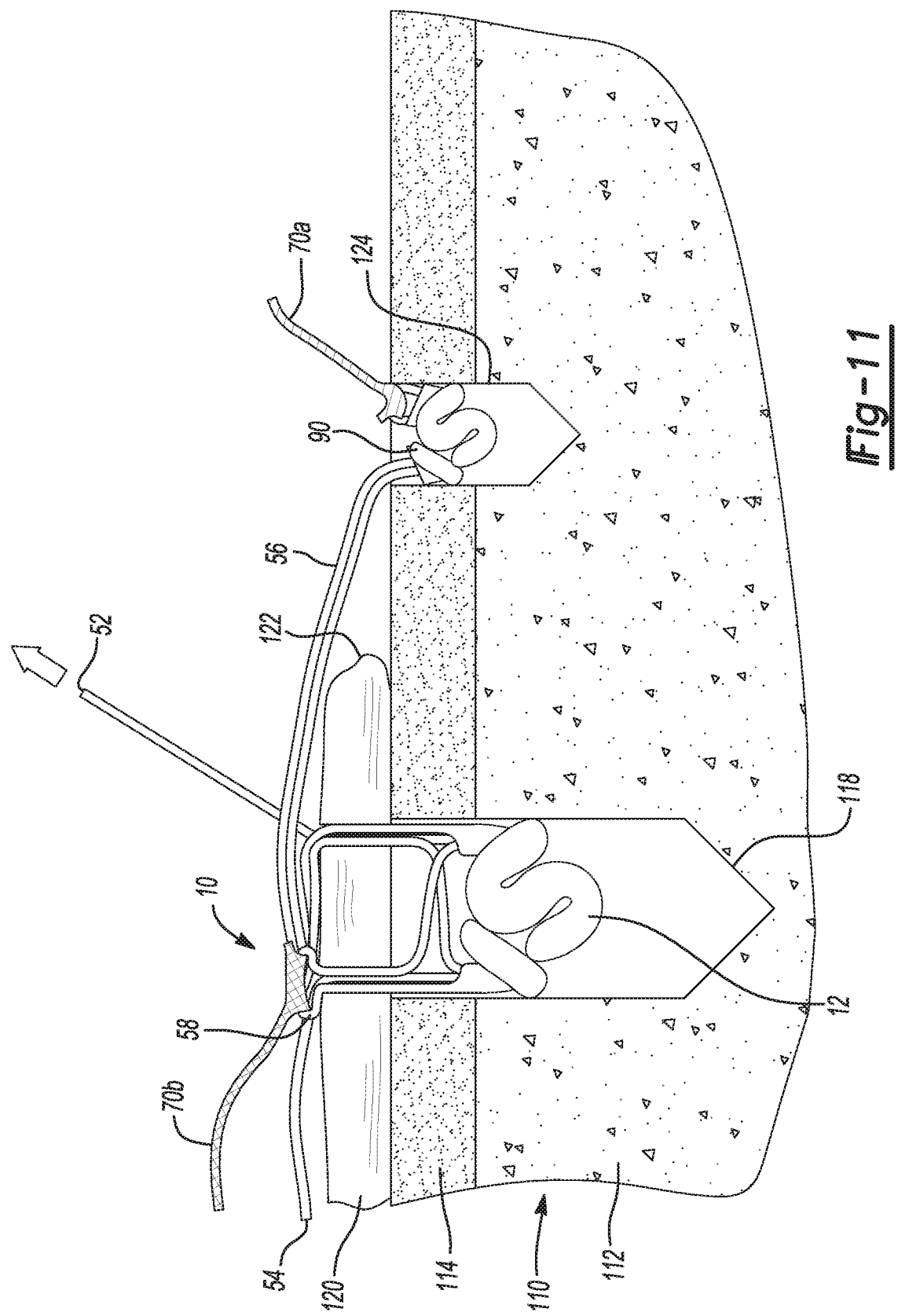
FIG. 11 illustrates the tissue fixation device of FIG. 1 implanted in bone to secure tissue to bone, and the additional anchor of FIG. 10 implanted in bone to facilitate tissue fixation and tensioning.

With reference to FIGS. 10 and 11, an additional soft or flexible anchor 90 may be added to the tissue fixation device 10 in order to provide additional fixation of the tissue 120. The anchor 90 may be similar to the anchor 12, or any other suitable soft or flexible anchor that is deformable in order to be retained in the bone hole 124. The anchor 90 can be added to the tissue fixation device 10 in any suitable manner, such as with a threader 130 illustrated in FIG. 10. The threader 130 includes a loop portion 132 at a distal end of elongated rods 134. The anchor 90 is initially seated on the elongated rods 134 such that the elongated rods 134 extend through the anchor 90.

The anchor 90 can be attached to the first suture tail 70a by first passing the tail portion 78a thereof into the loop portion 132, and folding the tail portion 78a over the loop portion 132. The anchor 90 is then slid over the tail portion 78a that is folded over the loop portion 132, and onto the first suture tail 70a. The first suture tail 70a and the first adjustable loop 56 coupled thereto are then pulled through the anchor 90 so that the anchor 90 is seated on the first adjustable loop 56. The anchor 90 can be implanted in the bone 110 in bone hole 124 beyond the distal end 122 of the tissue 120, as illustrated in FIG. 11. As the first end 52 of the suture strand 50 is pulled, the first adjustable loop 56 will shorten, thus drawing the first suture tail 70a against the anchor 90, and deforming the anchor 90 so that the anchor 90 will be retained in the bone 110. The first adjustable loop 56 will also span and contact the distal end 122 of the tissue 120 in order to retain the distal end 122 to the bore 110. The first end 72a of the first suture tail 70a will catch on an end of the anchor 90 and the first adjustable loop 56 will pull the second adjustable loop 58, as well as the tissue 120, towards the anchor 90, thereby tensioning the tissue 120 in the anterior to posterior direction, for example.

Figure 12:
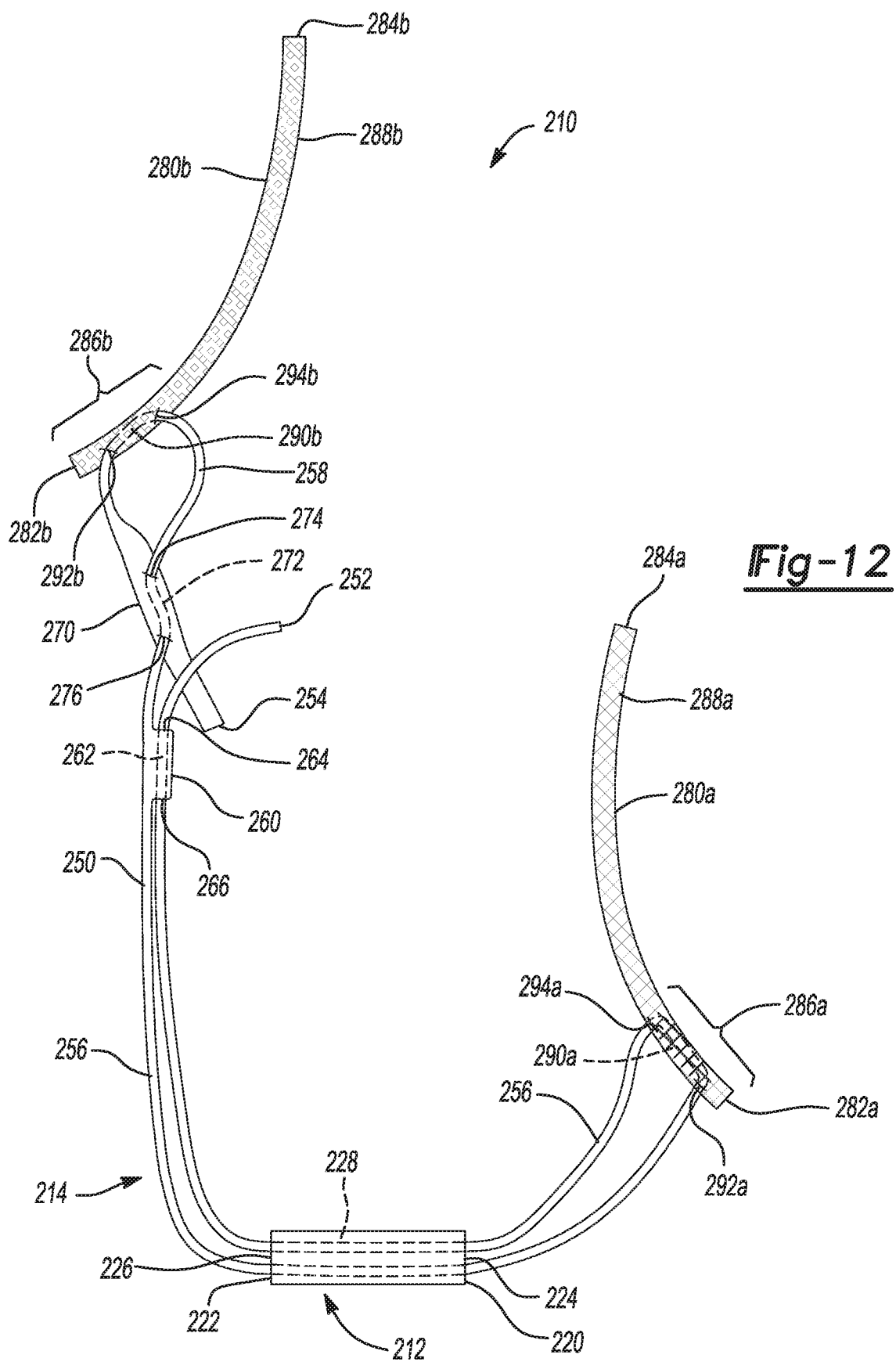
FIG. 12 illustrates another tissue fixation device according to the present teachings, with an anchor positioned on a suture construct of the tissue fixation device.

With reference to FIG. 12, another tissue fixation device according to the present teachings is illustrated at numeral 210. The tissue fixation device 210 generally includes a soft or flexible anchor 212 and a self-locking construct 214. The soft or flexible anchor 212 can be any suitable anchor, such as the anchor 12 described above, or any suitable alternate configurations thereof, such as the alternate configurations described above. The anchor 212 generally includes a first end 220 and a second end 222, which is opposite to the first end 220. The anchor 212 defines a first opening 224 at the first end 220, and a second opening 226 at the second end 222. An anchor internal passage 228 extends through the anchor 212 between the first opening 224 and the second opening 226.

The self-locking construct 214 can be any suitable self-locking construct, such as a construct including a suture 250. Alternately, the construct 214 can be any of the alternate constructs described above with respect to the construct 14. The suture 250 generally includes a first end 252 and a second end 254, which is opposite to the first end 252. The construct 214 defines a first loop 256 and a second loop 258, which are formed as described below.

A first body portion 260 of the suture 250 is generally between the first loop 256 and the second loop 258, and defines a passageway 262 extending between a first end 264 and a second end 266, through which the suture 250 extends to define the first loop 256. The first loop 256 extends from the first body portion 260. The suture 250 further includes a second body portion 270 proximate to the second end 254. The second body portion 270 defines a passageway 272 extending between a first opening 274 and a second opening 276 through which the suture 250 extends to define the second loop 258. The second loop 258 extends from the second body portion 270. The anchor 212 is seated on the first loop 256, such that portions of the suture 250 defining the first loop 256 extend through the anchor internal passage 228.

The tissue fixation device 210 further includes a first tail 280a and a second tail 280b. The first tail 280a is coupled to the first loop 256, and the second tail 280b is coupled to the second loop 258. The first and second tails 280a and 280b can be made of any suitable material, such as braided hollow-core suture. The first and second tails 280a and 280b can also be made of the same material that the first and second suture tails 70a and 70b of FIG. 1 are made of.

The first tail 280a is substantially similar to, or the same as, the second tail 280b. Therefore, the description of the first tail 280a also applies to the second tail 280b. Features in common between the first tail 280a and the second tail 280b are illustrated and described using like reference numbers, with the features of the first tail 280a including the suffix "a" and the features of the second tail 280b including the suffix "b." To facilitate distinguishing between the first and second tails 280a and 280b, such as by a surgeon in an operating room, the first and second tails 280a and 280b can include any suitable distinguishing features. For example, the first tail 280a can have a different color, pattern, design, length or width as compared to the second tail 280b.

The first tail 280a includes a first end 282a and a second end 284a, which is opposite to the first end 282a. Proximate to the first end 282a is a locking member/portion 286a. Extending from the locking member portion 286a to the second end 284a is a first tail portion 288a. The first tail 280a defines a passageway 290a at the locking member portion 286a. The passageway 290a extends between a first opening 292a and a second opening 294a of the first tail 280a. The first loop 256 extends through the passageway 290a. The first tail 280a and the second tail 280b can be used to adjust the sizes of the first and the second loops 256 and 258 respectively, as described herein with respect to FIGS. 22A-22O.

The first loop 256 can be made smaller by pulling the first end 252 through the passageway 262, thereby pulling a portion of the suture 250 proximate to the first end 252 through the passageway 262. The second loop 258 can be made smaller by pulling the second end 284b of the second tail 280b away from the passageway 272 so as to slide the second body portion 270 towards the second tail 280b. Although the second loop 258 is illustrated as an adjustable loop, the second loop 258 can be a rigid loop fixedly secure at the second body portion 270, for example, so as to restrict the second loop 258 from opening or closing.

The tissue fixation device 210 can be implanted in bone 110 in any suitable manner, such as described above with respect to the tissue fixation device 10 in FIG. 2. The tissue fixation device 210 can be used to secure tissue 120 to the bone 110 in any suitable manner, such as described above with respect to the tissue fixation device 10. For example, the anchor 212 can be seated into the bone hole 118 and then the first and second tails 280a and 280b can be passed through the tissue 120. The first tail 280a can be passed through the second loop 258, so as to arrange the first loop 256 such that a portion thereof extends through the second loop 258. The first loop 256 can be made smaller so as to press against and onto the tissue 120 by pulling the first end 252, which reduces the length of the first loop 256.

As the first end 252 is pulled, the locking member/portion 286a engages the second loop 258, so as to prevent the first tail 280a from passing back through the second loop 258. Furthermore, tension between the portion of the suture 250 extending through the passageway 262 and an interior of the passageway 262 causes the passageway 262 to collapse on the suture 250 and prevent the first loop 256 from reopening. If the second loop 258 is provided as a flexible loop, the second loop 258 may be made smaller by pulling the second tail 280b. Tension between the portion of the suture 250 extending through the passageway 272 and an interior of the passageway 272 cause the passageway 272 to collapse onto the suture 250 and prevent the second loop 258 from reopening.

Figure 13:
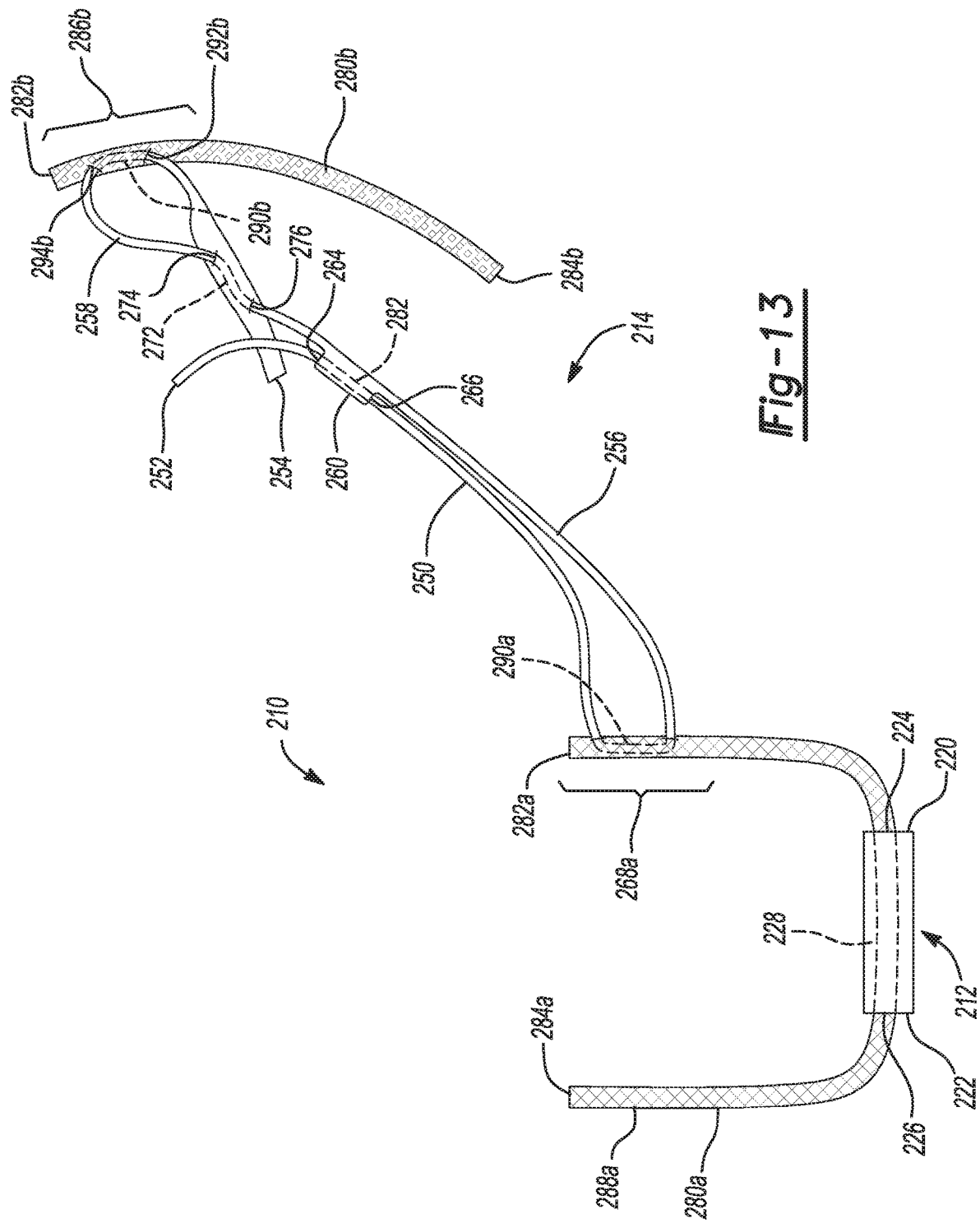
FIG. 13 illustrates the tissue fixation device of FIG. 12 with the anchor positioned on a tail of the tissue fixation device.

Although FIG. 12 illustrates the tissue fixation device 210 with the anchor 212 on the first loop 256, the anchor 212 of the tissue fixation device 210 can be initially seated on the first tail 280a, as illustrated in FIG. 13, such that the first tail portion 288a extends through the anchor internal passage 228. With reference to FIGS. 14-18, use of the tissue fixation device 210 of FIG. 13 with the anchor 212 initially seated on the first tail 280a to secure tissue 120 to the bone 110 will now be described. In applications where the anchor 212 is initially seated on the first loop 256, as illustrated in FIG. 12, the method of FIGS. 14-18 may also be used to secure tissue 120 to bone 110.

The anchor 212 is initially implanted in the bone hole 118, and the first tail 280a is passed through the tissue 120. A cannula 310 is arranged such that it extends through a patient's outer skin layer to facilitate introduction of the tissue fixation device 210 to an implant site, and to facilitate manipulation of the tissue fixation device 210 outside of the patient's body. By arranging the anchor 212 on the first tail 280a as opposed to on the first loop 256 as illustrated in FIG. 12, the construct 214 can remain outside of the joint space during much of the procedure to facilitate management of the fixation device 210, and particularly management of the construct 214.

Figure 14:
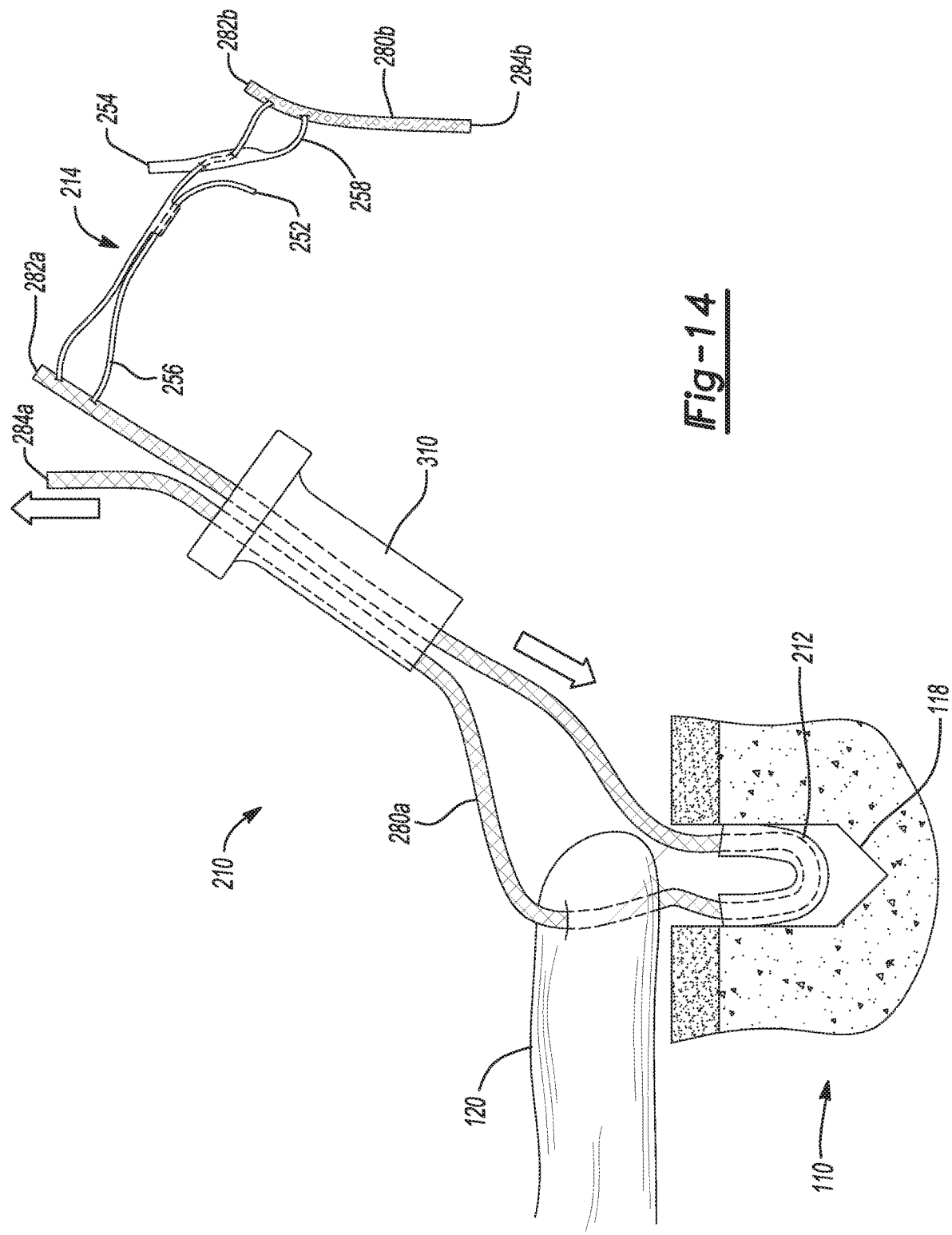
Figure 15:
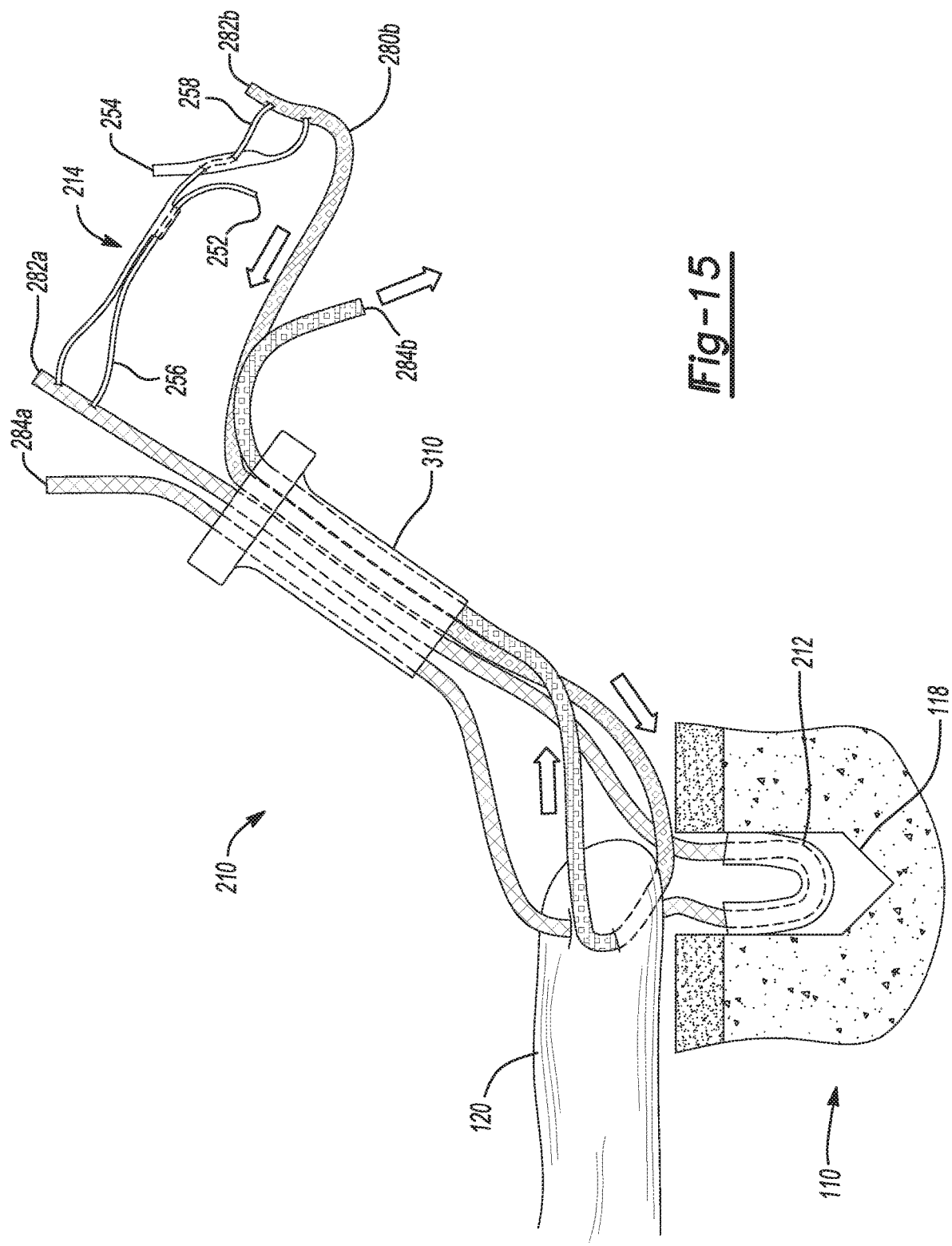
Figure 16:
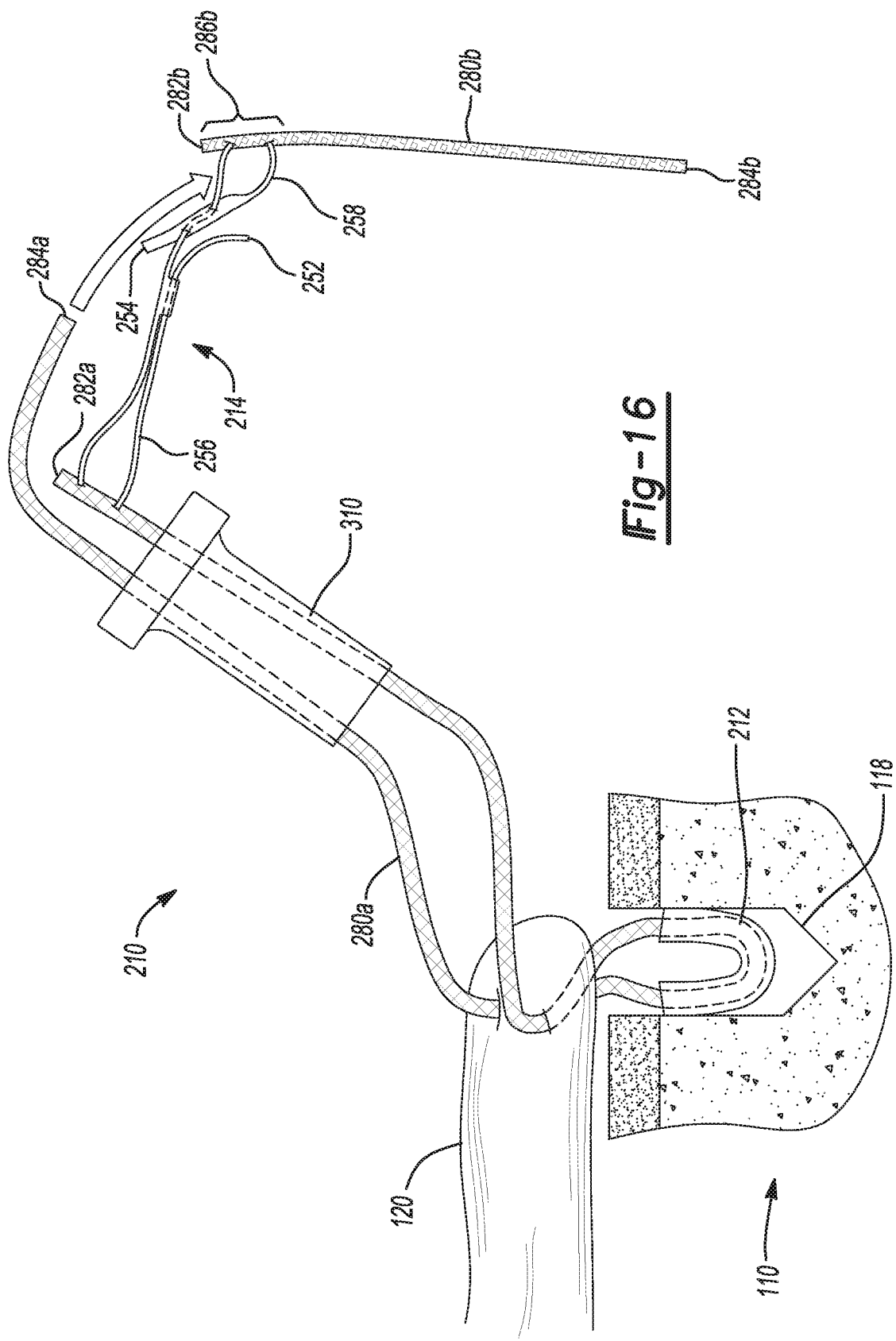

After the first tail 280a is passed through the tissue 120 as illustrated in FIG. 14, the second tail 280b is passed through the cannula 310, through the tissue 120, and back through the cannula 310, as illustrated in FIG. 15. With reference to FIG. 16, the first tail 280a is then passed through the second loop 258. Passing the first tail 280a through the second loop 258 draws the construct 214 through the cannula 310 and into engagement with the tissue 120, as illustrated in FIG. 17. More specifically, the first tail 280a is pulled until it completely passes through the tissue 120 and pulls the first loop 256 through the anchor 212 and up from the anchor 212 through the tissue 120. Pulling the first tail 280a also positions the second tail 280b at the tissue 120 such that the locking member/portion 286b abuts the tissue. To close the first loop 256 and secure the tissue 120 against the bone 110, the first end 252 of the suture 250 is pulled, as illustrated in FIG. 17. Excess portions of the first and second tails 280a and 280b can be removed after the first loop 256 has been completely zipped down, as illustrated in FIG. 18 for example. Thus, with the tissue fixation device 210, only a single suture strand need be pulled to close and tighten the construct 214 against the tissue 120.

A single tissue fixation device 210 can be used to secure the tissue 120 to the bone 110, or multiple tissue fixation devices 210 can be used. For example, multiple tissue fixation devices 210 can be individually implanted and not connected to each other, similar to the arrangement illustrated in FIG. 3 with respect to the tissue fixation device 10. Alternatively, multiple ones of the tissue fixation device 210 can be linked together, similar to the arrangement of FIGS. 3 and 8 with respect to the tissue fixation device 10. Thus, the first loop 256 of the tissue fixation device 210 can be coupled to the second loop 258 of a neighboring tissue fixation device 210 by inserting the first tail 280a through the second loop 258 of the neighboring tissue fixation device. Furthermore, the first or second tails 280a or 280b can be coupled to an anchor, which then may be implanted in bone, similar to that which is illustrated in FIG. 11 with respect to the tissue fixation device 10.

Figure 19:
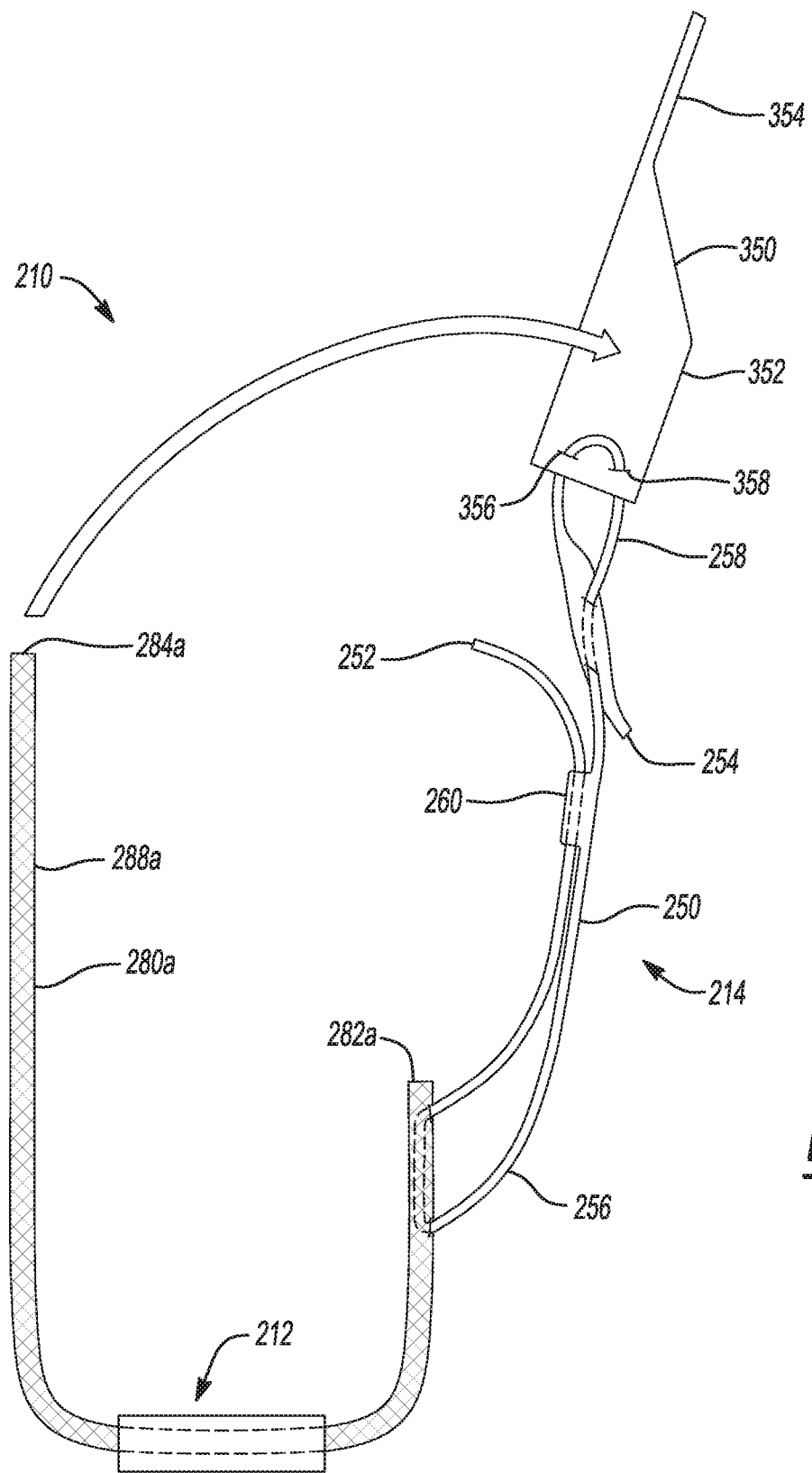
FIG. 19 illustrates the tissue fixation device of FIG. 13 including a braided strip.

With additional reference to FIG. 19, the tissue fixation device 210 can include a second tail in the form of a braided strip 350. The braided strip 350 can be made of any suitable material, such as suture, or of any of the alternatives described above with respect to the suture strands 50 and 250. The braided strip 350 generally includes a flat braided portion 352 and a round braided portion 354, as viewed in cross-section, extending from the flat braided portion 352.

The flat braided portion 352 defines a first opening 356 and a second opening 358. As illustrated in FIG. 19, the second loop 258 passes through the first and second openings 356 and 358 in order to secure the braided strip to the second loop 258. However, the second loop 258 is optional and thus need not be included. When the tissue fixation device 210 does not include the second loop 258, the braided strip 350 can be coupled to the suture 250 without a loop, such as with a knot or any other suitable coupling configuration. The braided strip 350 may also be unitary with the rest of the suture 250.

Instead of passing the first tail 280a through the second loop 258, the first tail can be passed through the flat braided portion 352 of the braided strip 350. As a result, when the first loop 256 is made smaller, as was described above in connection with FIG. 17, the braided strip 350 will extend across the tissue 120 in order to dissipate load applied to the tissue 120 by the tissue fixation device 210. The round braided portion 354 expands the distance that the braided strip 350 will extend across the tissue 120, thereby further dissipating load.

FIG. 19 illustrates the braided strip 350 (without the round braided portion 354) as included with the tissue fixation device 210 prior to being introduced to an implant site. However, the braided strip 350 may be added to the fixation device 210 after the first loop 256 has been passed through the tissue, as illustrated at FIG. 20. For example, the braided strip 350 may be arranged at the second end 284a of the first tail 280a and at the second end 284b of the second tail 280b. The first and second ends 282a and 284b may be passed through the braided strip 350, and the braided strip 350 may be slid down and across each of the first and second tails 280a and 280b using a pusher device 380 until the braided strip 350 passes over the first ends 282a and 282b of the first and second tails 280a and 280b respectively. After the first end 252 of the suture 250 is pulled to close the first loop 256, excess portions of the first and second tails 280a and 280b may be removed, as illustrated in FIG. 21.

With reference to FIGS. 22A-22C, when the tissue fixation device 210 is provided with the second loop 258 as an adjustable loop, the second loop 258 can be moved from an intermediate position illustrated in FIG. 22A to a closed position illustrated in FIG. 22B by pulling a portion of the suture 250 extending beyond the second body portion 270 in the direction of the first end 252 (direction A), and pulling the second end 284b of the second tail 280b in generally the opposite direction (direction B). To reopen the second loop 258, the second end 254 of the suture 250 is pulled in direction C and the second end 284b of the second tail 280b is pulled in direction D, as illustrated in FIG. 22C. Being able to selectively open and close the second loop 258 is advantageous for a number of reasons. For example, if the second loop 258 is accidentally closed prematurely, the second loop 258 can easily be reopened, such as to permit passage of the first tail 280a therethrough.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tissue fixation system, comprising:
a tissue fixation device, comprising:
a flexible tubular anchor; and
a single suture arranged into a self-locking suture construct, the single suture extending through a passage in the flexible tubular anchor to couple the self-locking suture construct to the flexible tubular anchor, the self-locking suture construct including a first adjustable loop, a second adjustable loop, and a first free end, wherein the first free end can be pulled to close the first adjustable loop;
a first flexible tail coupled to the first adjustable loop, the first flexible tail including a first elongated free tail portion that can be pulled to open the first adjustable loop; and
a second flexible tail coupled to the second adjustable loop, the second flexible tail including a second elongated free tail portion that can be pulled to open the second adjustable loop; and
an arthroscopic cannula,
wherein the first elongated free tail portion of the first flexible tail and the second elongated free tail portion of the second flexible tail extend longitudinally through the arthroscopic cannula from a first open end of the arthroscopic cannula to a second open end of the arthroscopic cannula.

2. The tissue fixation system of claim 1, wherein the passage in the flexible tubular anchor extends longitudinally within the flexible tubular anchor.

3. The tissue fixation system of claim 1, wherein the first adjustable loop and the second adjustable loop are spaced apart from one another in the self-locking suture construct.

4. The tissue fixation system of claim 1, wherein the single suture includes a second free end that can be pulled to close the second adjustable loop.

5. The tissue fixation system of claim 1, wherein the first flexible tail comprises a hollow core suture, and wherein the first flexible tail being coupled to the first adjustable loop includes suture of the first adjustable loop extending longitudinally through the hollow core suture.

6. The tissue fixation system of claim 1, wherein the flexible tubular anchor is an elongated tube.

7. The tissue fixation system of claim 1, wherein at least one of the first flexible tail and the second flexible tail comprises a braided suture.

8. The tissue fixation system of claim 7, wherein the braided suture includes a flat braided portion and a round braided portion.

9. A tissue fixation device, comprising:
a flexible tubular anchor; and
a single suture arranged into a self-locking suture construct, the single suture extending through a passage in the flexible tubular anchor to couple the self-locking suture construct to the flexible tubular anchor, the single suture including a first portion that extends through a first longitudinal passage in the single suture to form a first adjustable loop and a second portion that extends through a second longitudinal passage in the single suture to form a second adjustable loop, the first longitudinal passage and the second longitudinal passage longitudinally spaced apart from one another along the single suture, the single suture further including a first free end that can be pulled to close the first adjustable loop;
a first flexible tail coupled to the first adjustable loop, the first flexible tail including a first elongated free tail portion that can be pulled to open the first adjustable loop; and
a second flexible tail coupled to the second adjustable loop, the second flexible tail including a second elongated free tail portion that can be pulled to open the second adjustable loop,
wherein the first elongated free tail portion and the second elongated free tail portion are each of sufficient length to extend longitudinally through an arthroscopic cannula to an implant site from an outer skin layer of a patient,
wherein at least one of the first flexible tail and the second flexible tail comprises a braided suture that includes a flat braided portion and a round braided portion.

10. The tissue fixation device of claim 9 in combination with an arthroscopic cannula, wherein the first elongated free tail portion of the first flexible tail and the second elongated free tail portion of the second flexible tail extend longitudinally through the arthroscopic cannula from a first open end of the arthroscopic cannula to a second open end of the arthroscopic cannula.

11. The tissue fixation device of claim 9, wherein the first adjustable loop and the second adjustable loop are looped through one another.

12. The tissue fixation device of claim 9, wherein the first flexible tail comprises a hollow core suture, and wherein the first flexible tail being coupled to the first adjustable loop includes suture of the first adjustable loop extending longitudinally through the hollow core suture.

13. The tissue fixation device of claim 9, wherein the passage in the flexible tubular anchor extends longitudinally within the flexible tubular anchor.

14. The tissue fixation device of claim 9, wherein the single suture includes a second free end that can be pulled to close the second adjustable loop.

15. A tissue fixation system, comprising:
- a tissue fixation device, comprising:
  - a flexible tubular anchor; and
  - a single suture arranged into a self-locking suture construct, the single suture extending through a passage in the flexible tubular anchor to couple the self-locking suture construct to the flexible tubular anchor, the single suture including a first portion that extends through a first longitudinal passage in the single suture to form a first adjustable loop and a second portion that extends through a second longitudinal passage in the single suture to form a second adjustable loop, the single suture further including a first free end that can be pulled to close the first adjustable loop;
- a first flexible tail coupled to the first adjustable loop, the first flexible tail including a first elongated free tail portion that can be pulled to open the first adjustable loop; and
- a second flexible tail coupled to the second adjustable loop, the second flexible tail including a second elongated free tail portion that can be pulled to open the second adjustable loop,
- an arthroscopic cannula,
- wherein the first elongated free tail portion of the first flexible tail and the second elongated free tail portion of the second flexible tail extend longitudinally through the arthroscopic cannula from a first open end of the arthroscopic cannula to a second open end of the arthroscopic cannula.

16. The tissue fixation system of claim 15, wherein the first longitudinal passage is separate from the second longitudinal passage in the single suture.

17. The tissue fixation system of claim 15, wherein the first longitudinal passage is longitudinally spaced apart from the second longitudinal passage along the single suture.

18. The tissue fixation system of claim 15, wherein the single suture includes a second free end that can be pulled to close the second adjustable loop.

19. The tissue fixation system of claim 15, wherein the first flexible tail comprises a hollow core suture, and wherein the first flexible tail being coupled to the first adjustable loop includes suture of the first adjustable loop extending longitudinally through the hollow core suture.

20. The tissue fixation system of claim 15, wherein at least one of the first flexible tail and the second flexible tail comprises a flat braided suture portion and a round braided suture portion.

* * * * *